(12) United States Patent
Flake et al.

(10) Patent No.: US 10,864,131 B2
(45) Date of Patent: *Dec. 15, 2020

(54) EXTRACORPOREAL LIFE SUPPORT SYSTEM AND METHODS OF USE THEREOF

(71) Applicant: The Children's Hospital of Philadelphia, Philadelphia, PA (US)

(72) Inventors: Alan Flake, Philadelphia, PA (US); Emily Partridge, Philadelphia, PA (US); Marcus Davey, Philadelphia, PA (US)

(*) Notice: Subject to any disclaimer, the term of this patent is extended or adjusted under 35 U.S.C. 154(b) by 31 days.

This patent is subject to a terminal disclaimer.

(21) Appl. No.: 16/107,115

(22) Filed: Aug. 21, 2018

(65) Prior Publication Data
US 2019/0008712 A1      Jan. 10, 2019

Related U.S. Application Data

(63) Continuation of application No. 14/774,378, filed as application No. PCT/US2014/030277 on Mar. 17, 2014, now Pat. No. 10,085,907.

(60) Provisional application No. 61/788,052, filed on Mar. 15, 2013.

(51) Int. Cl.
*A61G 11/00* (2006.01)
*A61M 1/16* (2006.01)

(52) U.S. Cl.
CPC ............ *A61G 11/00* (2013.01); *A61M 1/1698* (2013.01); *A61M 1/168* (2013.01); *A61M 2205/3331* (2013.01); *A61M 2205/3334* (2013.01); *A61M 2205/3368* (2013.01); *A61M 2205/7518* (2013.01); *A61M 2240/00* (2013.01)

(58) Field of Classification Search
CPC .... A61M 1/1698; A61M 1/3601–3606; A61M 2240/00; A61M 2205/7518; A61G 11/00–009
See application file for complete search history.

(56) References Cited

U.S. PATENT DOCUMENTS

| | | |
|---|---|---|
| 2,723,660 A | 11/1955 | Greenberg |
| 4,048,684 A | 9/1977 | Korner et al. |
| 4,509,505 A | 4/1985 | Mercey et al. |

(Continued)

FOREIGN PATENT DOCUMENTS

| | | |
|---|---|---|
| CN | 203663028 U | 6/2014 |
| EP | 0447256 A2 | 9/1991 |

(Continued)

OTHER PUBLICATIONS

Zapol et al., Artificial Placenta: Two Days of Total Extrauterine Support of the Isolated Premature Lamb Fetus, Oct. 1969, Science 166:617-618.

(Continued)

*Primary Examiner* — Thaddeus B Cox
(74) *Attorney, Agent, or Firm* — BakerHostetler

(57) ABSTRACT

Extracorporeal membrane oxygenation systems and methods of use are disclosed. Several publications and patent documents are cited throughout the specification in order to describe the state of the art to which this invention pertains. Full citations of these references can be found throughout the specification. Each of these citations is incorporated herein by reference as though set forth in full.

16 Claims, 17 Drawing Sheets

(56) References Cited

U.S. PATENT DOCUMENTS

| | | | |
|---|---|---|---|
| 4,617,912 | A | 10/1986 | Beer et al. |
| 4,796,605 | A | 1/1989 | Sasaki et al. |
| 5,063,924 | A | 11/1991 | Galvan et al. |
| 5,207,639 | A | 5/1993 | Cooper |
| 5,218,958 | A | 6/1993 | Cooper |
| 5,308,310 | A | 5/1994 | Roff et al. |
| 6,611,978 | B1 | 9/2003 | Schmidt et al. |
| 2001/0033813 | A1 | 10/2001 | Filho et al. |
| 2004/0133064 | A1 | 7/2004 | Castillon et al. |
| 2004/0193096 | A1 | 9/2004 | Cooper |
| 2005/0124850 | A1 | 6/2005 | Mackin |
| 2007/0010005 | A1 | 1/2007 | Sitzmann |
| 2008/0014622 | A1* | 1/2008 | Federspiel ........... B01D 69/145 435/182 |
| 2010/0101657 | A1* | 4/2010 | Morley ............... A61M 1/1698 137/14 |
| 2010/0168502 | A1 | 7/2010 | Delaporte et al. |
| 2012/0226258 | A1* | 9/2012 | Otto ..................... A61M 1/3489 604/500 |
| 2013/0274543 | A1 | 10/2013 | Matsubara et al. |
| 2016/0022524 | A1 | 1/2016 | Flake et al. |
| 2017/0128322 | A1 | 5/2017 | Fassihi et al. |

FOREIGN PATENT DOCUMENTS

| | | |
|---|---|---|
| JP | 08-294519 A | 11/1996 |
| JP | 2013-233194 A | 11/2013 |
| RU | 2376969 C1 | 12/2009 |
| WO | 2006/125955 A1 | 11/2006 |
| WO | 2013/026148 A1 | 2/2013 |
| WO | 2013/029044 A1 | 2/2013 |

OTHER PUBLICATIONS

Yasufuku et al., Arterio-venous extracorporeal membrane oxygenation of fetal goat incubated in artificial amniotic fluid (Artificial placenta): Influence on lung growth and maturation, Mar. 1998, J. Pediatr. Surg., 33:442-448.

Walker et al., Impairment of cerebral autoregulation during venovenous extracorporeal membrane oxygenation in the newborn lamb, Dec. 1996, Crit. Care Med., 24:2001-2006.

Vutskits, L., Cerebral blood flow in the neonate, 2014, Pediatr. Anesth., 24:22-29.

Unno et al., Development of an Artificial Placenta: Survival of Isolated Goat Fetuses for Three Weeks with Umbilical Arteriovenous Extracroporeal Membrane Oxygenation, Dec. 1993, Artificial Organs 17:996-1003.

Unno et al., An Evaluation of the System to Control Blood flow in Maintaining Goat Fetuses on Arterio-Venous Extracorporeal membrane Oxygenation: A Novel Approach to the Development of an Artificial Placenta, Dec. 1997, Artificial Organs 21:1239-1246.

Stolar et al., Extracorporeal membrane oxygenation causes significant changes in intracranial pressure and carotid artery blood flow in newborn lambs, Dec. 1988, J. Pediatr. Surg., 23:1163-1168.

Short et al., Impairment of Cerebral Autoregulation during Extracorporeal Membrane Oxygenation in Newborn Lambs, 1993, Pediatr. Res., 33:289-294.

Schoberer et al, Miniaturization: the clue to clinical application of the artificial placenta, Mar. 2014, Artificial Organs 38:208-14.

Rochow et al, "Integrated Microfluidic Oxygenator Bundles for Blood Gas Exchange in Premature Infants", MEMS 2012, Paris, France, Jan. 2012, pp. 957-960.

Rochow et al, "Artificial Placenta—Lung Assist Devices for Term and Pre-term Newborns With Respiratory Failure", Int. J. Artif. Organs 2013; 36 (6) pp. 377-391.

Papademetriou et al., Wavelet Cross-Correlation to Investigate Regional Variations in Cerebral Oxygenation in Infants Supported on Extracorporeal Membrane Oxygenation, 2013, Adv. Exp. Med. Biol., 765:203-209.

Miura et al, "Novel Modification of an Artificial Placenta: Pumpless Arteriovenous Extracorporeal Life Support in a Premature Lamb Model", Pediatric Research, vol. 72, No. 5, Nov. 2012.

Martin et al., Preterm Births—United States, 2006 and 2010, MMWR Surveill. Summ., 62 (Suppl 3): 136-138, Nov. 2013.

Kuwabara et al., Development of Extrauterine Fetal Incubation System Using Extracorporeal Membrane Oxygenator, 1987, Artificial Organs 11:224-227.

Kuwabara et al., Artificial Placenta: Long-Term Extrauterine Incubation of Isolated Goat Fetuses, Dec. 1989, Artificial Organs 13:527-531.

Kumar et al., Post extracorporeal membrane oxygenation single photon emission computed tomography (SPECT) as a predictor of neurodevelopmental outcome, Jun. 1994, Pediatrics 93:951-955.

International Search Report and Written Opinion issued in International Application No. PCT/US14/30277 dated Aug. 11, 2014.

Ijsselstein et al., Long-term outcome of children treated with neonatal extracorporeal membrane oxygenation: Increasing problems with increasing age, Mar. 2014, Semin. Perinatol., 38:114-121.

Huddleston et al., Lung Transplantation in Children, 2002, Ann Surg., 236:270-276.

Hanif et al., Variables that affect the middle cerebral artery peak systolic velocity in fetuses with anemia and intrauterine growth restriction, Sep. 2007, Am. J. Perinatol., 24:501-505.

Faber et al., Foetal Placental Blood Flow in the Lamb, 1972, J. Pysiol., 223:375-393.

European Application 14763073, Supplementary European Search Report dated Jan. 4, 2017, 7 pages.

Crossley KJ, Nicol MB, Hirst JJ, Walker DW, Thorburn GD. Suppression of arousal by progesterone in fetal sheep. Reproduction, fertility and development. 1997;9(8):767-774.

Creasy et al., Determination of Fetal, Placental and Neonatal Blood Volumes in the Sheep, Oct. 1970, Circulation Research, Res., 27:487-494.

Callaghan et al., Studies in the Development of an Artificial Placenta, 1963, Circulation 27:686-690.

Boston et al., Paracorporeal lung assist device: An innovative surgical strategy for bridging to lung transplant in an infant with severe pulmonary hypertension caused by alveolar capillary dysplasia, Oct. 2013, J. Thorac. Cardiovasc. Surg., 146:e42-e43.

Behrman et al., ed., Institute of Medicine (US) Committee on Understanding Premature Birth and Assuring Healthy Outcomes; Washington DC: National Academies Press; 2007, 791 pages in three parts.

Awad et al., Pumpless Resipiratory Assistance Using a Membrane Oxygenator as an Artificial Placenta: A Preliminary Study in Newborn and Preterm Lambs, 1995, J. Invest. Surg., 8:21-30.

Arens et al, "NeonatOx: A Pumpless Extracorporeal Lung Support for Premature Neonates", Artificial Organs, vol. 35, No. 11, 2011, pp. 997-1001.

* cited by examiner

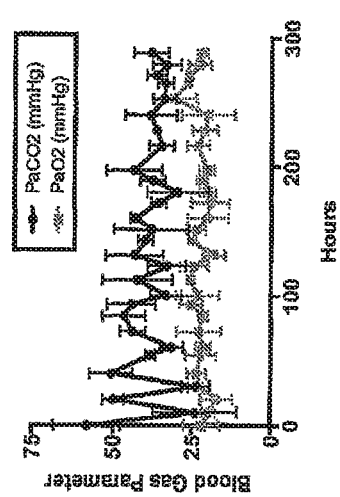
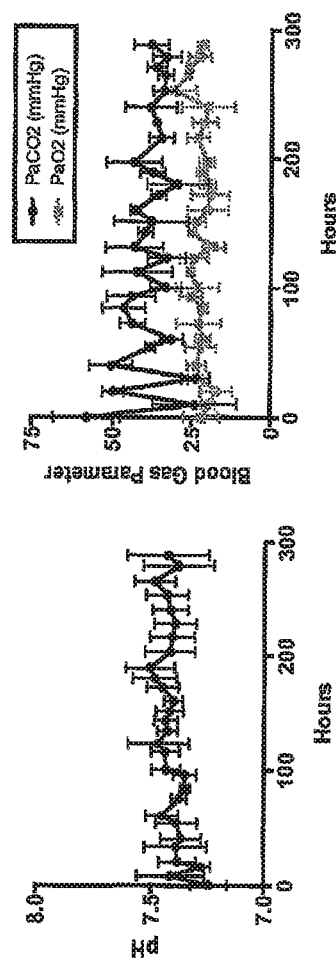
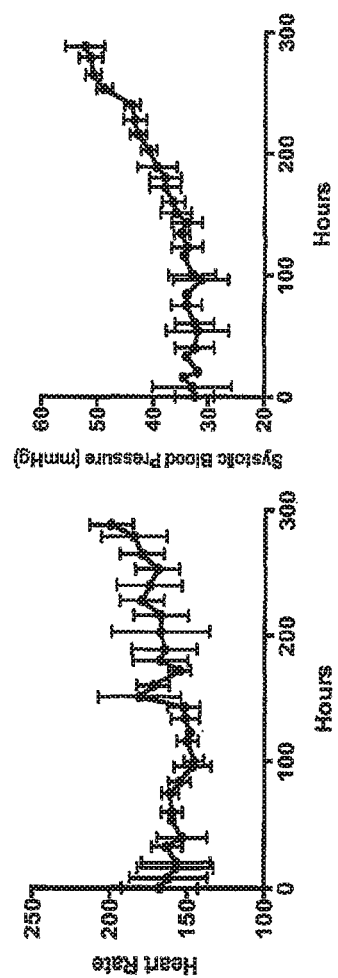
Fig. 8A  Fig. 8B  Fig. 8C  Fig. 8D

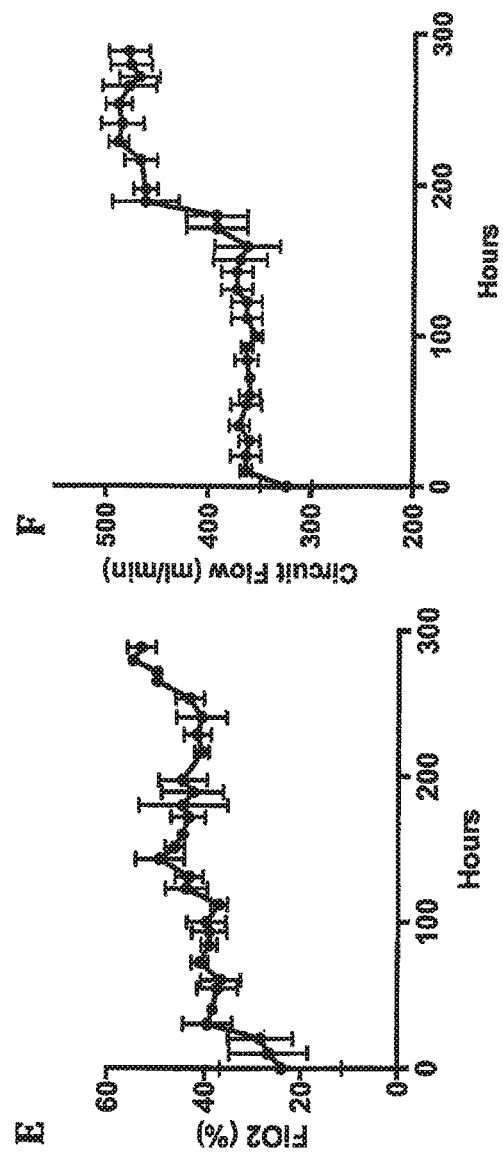

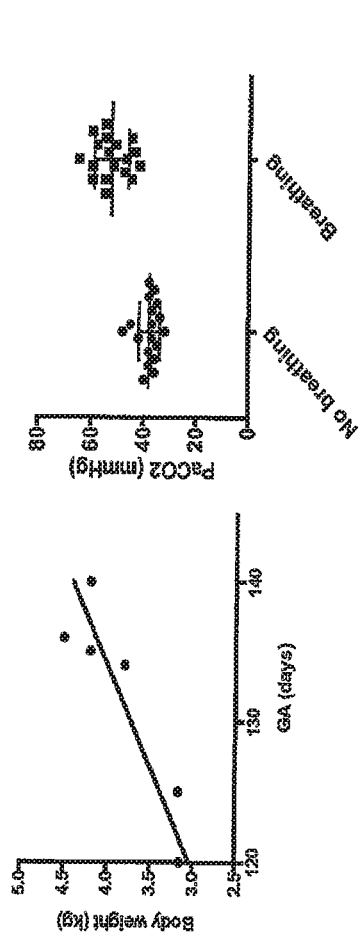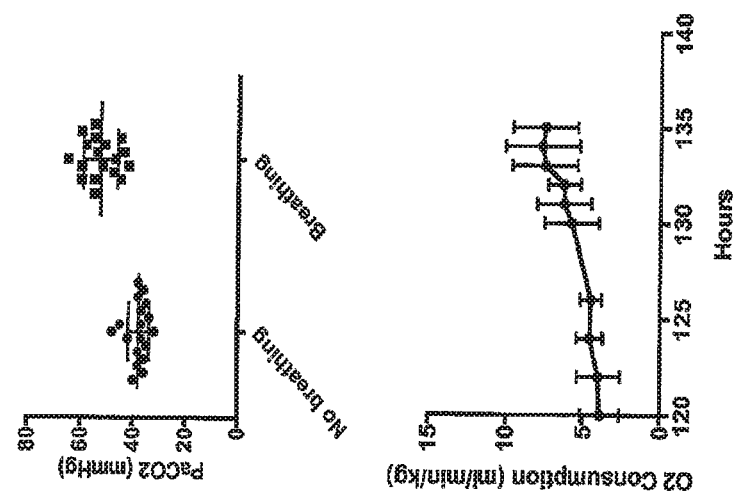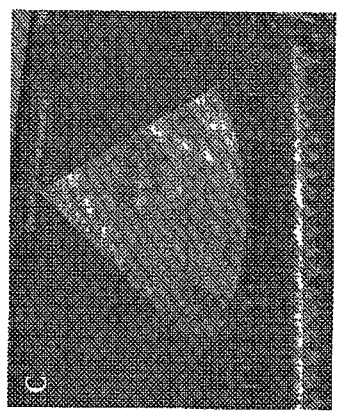
Fig. 10A  Fig. 10B  Fig. 10C  Fig. 10D

EXTRACORPOREAL LIFE SUPPORT SYSTEM AND METHODS OF USE THEREOF

CROSS REFERENCE TO RELATED APPLICATIONS

This application is a continuation of U.S. patent application Ser. No. 14/774,378 filed Sep. 10, 2015, now U.S. Pat. No. 10,085,907, which is a National Stage of International Application No. PCT/US2014/30277 filed Mar. 17, 2014, which claims the benefit of U.S. Provisional Patent Application No. 61/788,052, filed Mar. 15, 2013, the disclosures of which are incorporated by reference herein in their entireties.

TECHNICAL FIELD

The present invention relates to the field of neonatal care. More specifically, the invention provides apparati and methods for the maintenance of homeostasis in the pre-viable fetus outside of the womb.

BACKGROUND

Several publications and patent documents are cited throughout the specification in order to describe the state of the art to which this invention pertains. Full citations of these references can be found throughout the specification. Each of these citations is incorporated herein by reference as though set forth in full.

In cases of extreme prematurity, survival outside the womb is complicated by inadequate organogenesis, including insufficient lung growth and maturation to permit gas exchange. Furthermore, in the event of congenital anomalies affecting the growth and development of the lungs, such as congenital diaphragmatic hernia and other causes of pulmonary hypoplasia, insufficient pulmonary function may limit long-term survival. The development of an extracorporeal system to support ongoing fetal growth and development without the perturbations induced by postnatal intensive care, would offer a chance for survival of such infants with reduced mortality and long term morbidity. The ability to maintain homeostasis in the pre-viable fetus for weeks or months may also alter the current standards for assessment of viability outside the womb.

SUMMARY

In accordance with the instant invention, an extracorporeal membrane oxygenation system (artificial placenta) is provided. In a particular embodiment, the system is pumpless and comprises a very low resistance oxygenator. The system/apparatus may further comprise an incubation chamber for holding the subject and sterile liquid in which to submerge the subject. The system/apparatus may further comprise a pump and filtration system for the sterile liquid. Examples of a system/apparatus of the instant invention are shown in FIGS. 1 and 7A.

In accordance with another aspect of the instant invention, methods for the extracorporeal oxygenation of a subject (e.g., maintaining a fetus in an extrauterine setting to allow for growth and maturation) are provided. In a particular embodiment, the method comprises connecting the subject to the extracorporeal membrane oxygenation system of the instant invention. The subject may be connected to the oxygenator via vessels in the neck. In a particular embodiment, the subject is a premature fetus, extreme premature fetus, or a pre-viable fetus. In a particular embodiment, the oxygenator is primed with fetal blood. The subject may also be maintained submerged in an incubation chamber comprising sterile liquid, particularly where the sterile liquid is heated and continually pumped through a filtration system.

BRIEF DESCRIPTION OF THE DRAWINGS

FIG. 8A is a graph showing stability of fetal biochemical and hemodynamic parameters, specifically carotid arterial sampling for pH over the course of 300 hours with error bars representing five independent experiments.

FIG. 8B is a graph showing stability of fetal biochemical and hemodynamic parameters, specifically partial pressure of $CO_2$ and $O_2$ over the course of 300 hours with error bars representing five independent experiments.

FIG. 8C is a graph showing stability of fetal biochemical and hemodynamic parameters, specifically the recorded fetal heart rate over the course of 300 hours with error bars representing five independent experiments.

FIG. 8D is a graph showing stability of fetal biochemical and hemodynamic parameters, specifically systolic blood pressure over the course of 300 hours with error bars representing five independent experiments.

FIG. 8E is a graph showing stability of fetal biochemical and hemodynamic parameters, specifically delivery to the oxygenator over the course of 300 hours with error bars representing five independent experiments.

FIG. 8F is a graph showing stability of fetal biochemical and hemodynamic parameters, specifically carotid arterial sampling for pH over the course of 300 hours with error bars representing five independent experiments.

FIG. 10A shows fetal growth and metabolism with the instant invention, specifically weight gain over the course of fetal incubation.

FIG. 10B shows fetal growth and metabolism with the instant invention, specifically fetal breathing response to increased $PaCO_2$ levels.

FIG. 10C shows fetal growth and metabolism with the instant invention, specifically patency of the ductusarteriosis (white arrow) confirmed by fetal echocardiography.

FIG. 10D shows fetal growth and metabolism with the instant invention, specifically fetal oxygen consumption over the course of incubation.

DETAILED DESCRIPTION OF ILLUSTRATIVE EMBODIMENTS

Figure 1:
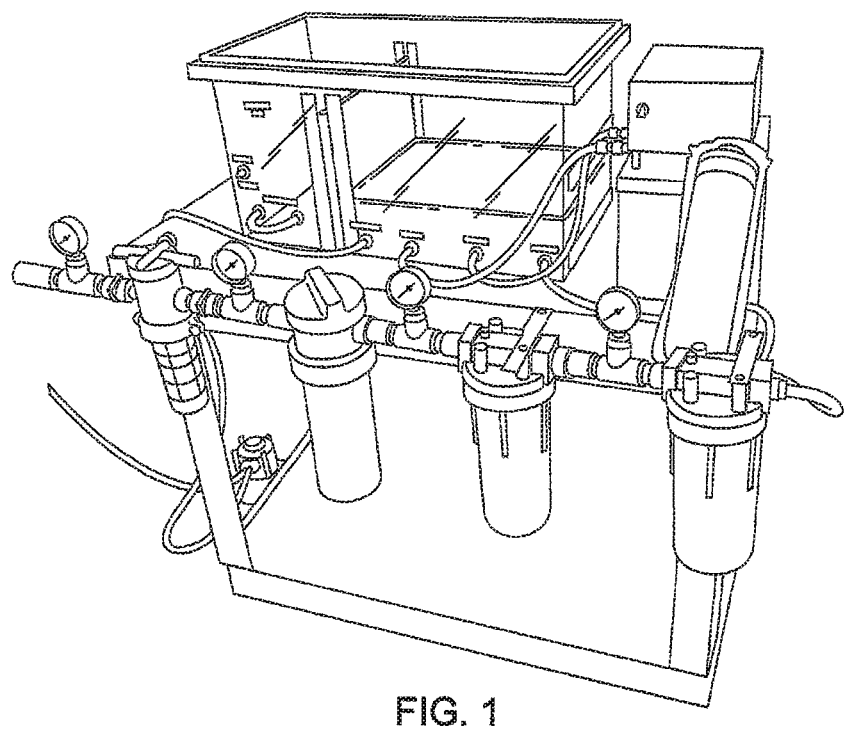
FIG. 1 is an isometric representation of an example of an apparatus of the instant invention.

Respiratory failure remains the major challenge to survival in the critically premature infant. The development of an extrauterine system to support ongoing fetal growth and development would represent a changing paradigm in the management of such patients. The concept of the artificial placenta was first introduced over 50 years ago, but numerous studies employing conventional pump-supported extracorporeal oxygenation systems have had limited success due to circulatory overload and cardiac failure. A pumpless oxygenation circuit has long been speculated to promise advantages over current ECMO technology, including reduced priming and distribution volumes, shorter exposure of blood to thrombogenic surfaces, and achieving innate regulation of blood flow and pressure by the fetal heart itself. However, the development of such a circuit remains elusive, with several well-designed studies resulting in rapid circulatory failure. Herein, complete physiologic support of extrauterine fetal lambs is reported with a pumpless artificial placenta, with stable hemodynamics, maintenance of fetal circulation, and normal growth and metabolism. This is the first successful demonstration of long-term maintenance of a fetus in an extrauterine environment with autoregulation of systemic circulation in a manner analogous to the fetal-placental circuit.

Premature birth may occur due to any one of a multitude of reasons. For example, premature birth may occur spontaneously due to preterm rupture of the membranes (PROM), structural uterine features such as shortened cervix, secondary to traumatic or infectious stimuli, or due to multiple gestations. Preterm labor and delivery is also frequently encountered in the context of fetoscopy or fetal surgery, where instrumentation of the uterus often stimulates uncontrolled labor despite maximal tocolytic therapy.

The 2010 CDC National Vital Statistics Report notes birth rates at a gestational age of less than 28 weeks in the U.S. over the past decade have remained stable at approximately 0.7%, or 30,000 births annually. Similarly, birth rates at gestational ages 28-32 weeks over the past decade in the U.S. have been stable at 1.2%, or 50,000 births annually. Patients with pulmonary hypoplasia secondary to congenital diaphragmatic hernia, oligohydramnios, or abdominal wall defects are also significant. The National Birth Defects Prevention Network reports an annual incidence of congenital diaphragmatic hernia between 0.9 to 5.8 per 10,000 live births in the U.S., or approximately 375-2,500 births annually. The incidence of other causes of pulmonary hypoplasia is not well documented.

The major physiologic limitation of the preterm infant affecting survival is pulmonary insufficiency due to insufficient pulmonary growth and maturation to permit gas exchange. The development of a system for extracorporeal oxygenation of the fetus would represent a major milestone towards a complete artificial placenta. Previous attempts to achieve adequate oxygenation of the fetus in animal models have employed traditional extracorporeal membrane oxygenation (EMOC) with pump support, and have been limited by circulatory overload and cardiac failure in treated animals. Reoma et al. (J. Ped. Surg. (2009) 44:53-59) describe an aterio-venous extracorporeal life support system using a low resistance oxygenator (MC3; Ann Arbor, Mich.). However, the pumpless system of Reoma et al. was unsuccessful as 2 of 7 fetuses dies within three hours and the remainder of the fetuses exhibited hemodynamic instability with fetal hypotension, bradycardia and acidosis within 4 hours. During the four hour period, Reoma et al. observed reduced device flow, reduced oxygen delivery, and reduced aortic flow over time and ultimately concluded that the inclusion of a pump was needed for adequate long term support.

The system of the instant invention allows for the support and ongoing growth and organ maturation of the fetus while maintaining fetal physiology in an extrauterine setting. The system substantially reduces the mortality, morbidity and costs associated with prematurity and complex lung lesions. Indeed, a 2007 report by the Institute of Medicine (Behrman et al., ed., Institute of Medicine (US) Committee on Understanding Premature Birth and Assuring Healthy Outcomes; Washington D.C.: National Academies Press; 2007) estimates the cost associated with preterm birth to be in excess of $26.2 billion in 2005 alone, with the majority of cost incurred during the initial medical management in the intensive care setting.

In accordance with the instant invention, the fetal heart is used to drive flow through the circuit and oxygenator (i.e., it is a pumpless system). The use of a pumpless system avoids exposure of the fetal heart to excess preload encountered in non-pulsatile pump-assisted circuits. The pumpless system also permits intrinsic fetal circulatory regulation of flow dynamics. The oxygenator of the instant invention is preferably very low resistance, has low priming volume and low transmembrane pressure drops, and provides efficient gas exchange. In a particular embodiment, the oxygenator has a pressure drop of less than about 50 mmHg or about 40 mmHg at 1.5 l/min of blood flow. In a particular embodiment, the priming volume of the oxygenator is less than about 100 ml, particularly less than about 85 ml. In a particular embodiment, the oxygenator has a blood flow range up to about 2.0 l/min, about 2.5 l/min, about 2.8 l/min, or greater. In a particular embodiment, the oxygenator has a gas transfer rate of about 150 ml/min, about 160 ml/min, about 180 ml/min, or greater for $O_2$. In a particular embodiment, the oxygenator is a hollow fiber membrane oxygenator (e.g., a polymethyl pentene hollow fiber membrane oxygenator). In a particular embodiment, the oxygenator is lined with anti-clotting measures/compounds (e.g., immobilized polypeptide and/or heparin). In a particular embodiment, the oxygenator is the Quadrox-iD™ pediatric oxygenator (Maquet; Wayne, N.J.).

The subjects of the instant invention may be infants, including term and preterm infants. The preterm infant may be premature infants (i.e., less than 37 weeks estimated gestational age, particularly 28-32 weeks), extreme premature infants (i.e., 24-28 weeks), or pre-viable fetuses (e.g., 20-24 weeks). The gestation periods are provided for humans, though corresponding preterm infants of other animals may be used. In a particular embodiment, the preterm infant has no underlying congenital disease. In a particular embodiment, the term or preterm infants has limited capacity for pulmonary gas exchange, for example, due to pulmonary hypoplasia or a congenital anomaly affecting lung development, such as congenital diaphragmatic hernia. In a particular embodiment, the subject is a preterm or term neonate awaiting lung transplantation, for example, due to congenital pulmonary disease (e.g., bronchioalveolar dysplasia, surfactant protein B deficiency, and the like). Such transplantation surgeries are currently rarely performed in the U.S. (Huddleston et al. (2002) Ann Surg., 236:270-6). However, the number of transplantation surgeries would be increased with the more stable method for pulmonary support provided by the instant invention. The subject may also be a candidate for ex utero intrapartum treatment (EXIT) delivery, including patients with severe airway lesions and a long expected course before definitive resection. The subject may also be a fetal surgical or fetoscopic procedure patient, particularly with preterm labor precipitating early delivery. The subject may be maintained in the apparatus of the instant invention for as long as needed (e.g., for days, weeks or months).

In a particular embodiment of the instant invention, cannulae are placed in the great neck vessels (e.g., carotid) of the subject to connect the circulatory system of the subject to the oxygenator. The placement in the great neck vessels avoids issues of vasospasm and cannula instability in umbilical vessels. The connective tubing (e.g., silicone) between the oxygenator and the cannulae is preferably as short and narrow as feasible in order to reduce blood volume outside the subject. However, the potential movements of the subject should be considered in the length of the tubing. In a particular embodiment, the tubing is about 12 inches or less from the cannula to the oxygenator. In a particular embodiment, the tubing is lined with anti-clotting measures/compounds (e.g., immobilized polypeptide and/or heparin) (i.e., the tubing is clot resistant). As explained hereinbelow, the external portion of the cannulas may be fitted with a sleeve (e.g., to permit increased tension of the stabilizing sutures). The sleeve may be made of silicone and may be, for example, about 1-10 cm in length, particularly about 3-5 cm in length. The cannulae may be sutured to the animal (e.g., via the fitted sleeve) to secure them to the neck of the animal.

In a particular embodiment of the instant invention, the oxygenator device is primed with blood. The oxygenator device may be primed with, for example, maternal blood and/or fetal blood. The priming of the oxygenator with fetal hemoglobin permits optimal oxygen exchange across the membrane. Indeed, the fetal oxygen dissociation curve is shifted to the left meaning that fetal arterial oxygen pressures are lower than adult arterial oxygen pressures. In a particular embodiment, the blood comprises heparin.

In a particular embodiment, the gas inflow to the oxygenator is mixed medical air and oxygen.

In a particular embodiment, the subject is placed with an incubator. In a particular embodiment, the incubator is a chamber filled with a sterile liquid such that the subject is submerged (e.g., approximating the in utero environment). The incubation chamber may be sealed to prevent contamination of the sterile liquid on the inside. In a particular embodiment, the top of the chamber is removable or is a lid to allow access to the subject. However, the top should be sealable to the remainder of the chamber (e.g., via a gasket).

In a particular embodiment, the chamber is a rigid structure such as a box or bowl made out of glass, metal, or an inert medical grade plastic or silicone. In a particular embodiment, the chamber is a bag or sac (e.g., made out of an inert medical grade plastic or silicone; water-tight), thereby replicating the amniotic sac. The chamber may comprise a hanging or suspended mesh or hammock to place the subject on within the chamber (see, e.g., FIGS. 11A and 11B). The hanging/suspended mesh (e.g., a sling or hammock) reduces fetal anxiety, thereby reducing fetal movement and possible disruption or disconnection of attached probes or cannulae. The hanging/suspended mesh (e.g., sling or hammock) may be made out of a sterile and inert medical grade material such as metal or nylon. The incubation chamber may also comprise glove ports to allow sterile access to the subject (e.g., for swaddling of the subject to calm or to gain access to objects within the interior of the chamber).

The sterile liquid within the incubation chamber may be amniotic fluid, sterile artificial/synthetic amniotic fluid, Lactated Ringer's solution, or the like. The sterile liquid may contain antibiotics (e.g., penicillin) and/or lysozyme. The sterile liquid and/or incubator may be heated to maintain the body temperature of the subject. The sterile liquid may be heated outside of the incubator and pumped in warm and/or may be heated within the chamber. In a particular embodiment, a warm liquid (e.g., water) is pumped into a closed unit (e.g., tubing (e.g., silicone), particularly in a loop or coiled shape) within the chamber and returned to a heater before being pumped in again. In a particular embodiment, the warm liquid is pumped into the heating coil at about 50° C.

Figure 4:
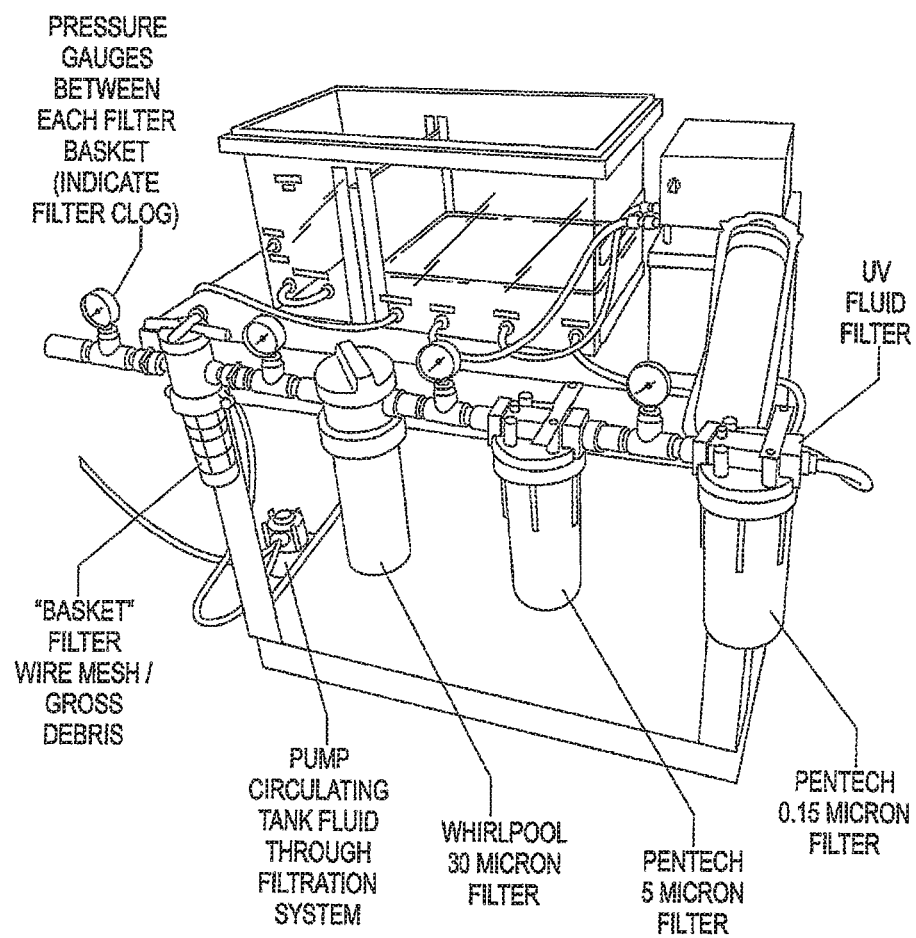
FIG. 4 is an isometric representation of a filtration system.

In a particular embodiment, the fluid within the incubator chamber is connected to a pump and one or more filters (e.g., to remove particulate matter excreted from the subject in the chamber). In a particular embodiment, the apparatus comprises a series of filters which may optionally have pressure gauges in between them to allow for rapid identification of any filter clogs. The filtration system may also comprise a UV fluid filter. An example of a filter system is shown in FIG. 4. Depicted in FIG. 4 is a gross debris filter connected in succession with a 30 micron filter, a 5 micron filter, and a 0.15 micron filter. The filtration system may comprise any number of filters of varying pore size. For example, the filtration system may comprise a gross debris filter connected in succession with a 1 micron filter, a 30 micron filter, a 1 micron filter, a 5 micron filter, 0.2 micron filter, and a 0.15 micron filter. An example of another filter system is shown in FIG. 7A wherein a pump is connected to a 100 μm filter and a UV light.

In a particular embodiment, the fluid within the incubator chamber is exchanged about 1 to about 10 times daily, particularly about 1 to about 5 times daily or about 2 to about 4 times daily. Sterile fluid may be pumped into the chamber by at least one port. Fluid may be removed from the chamber through at least one port, wherein the fluid may be removed from the chamber with the assistance of a pump. An example of the exchange system is shown in FIG. 7A, wherein a pump moves sterile fluid into the chamber at a first port and a second pump removes old fluid from the chamber through a second port. In a particular embodiment, the apparatus and methods of the instant invention use fluid exchange and/or filtration for maintaining the sterility of the fluid (e.g., fluid exchange may be used without supplemental filtration, although the combined use will increase sterility).

In a particular embodiment, the subject receives nutritional support through feeding tubes or IV while in the incubation chamber. The subject may also be administered sedatives in order to limit movements, but the instant invention does allow for some movements within the chamber so it may not be necessary. The subject may also be administered antibiotics (e.g., ampicillin, gentamycin, etc.). The subject may also be administered an anticoagulant (e.g., heparain). The subject may also be administered a prostaglandin (e.g., prostaglandin-E1 or E2). The subject's vital signs, weight, liver function, and blood flow are also typically monitored. Bilirubin levels may also be monitored.

Figure 7A:
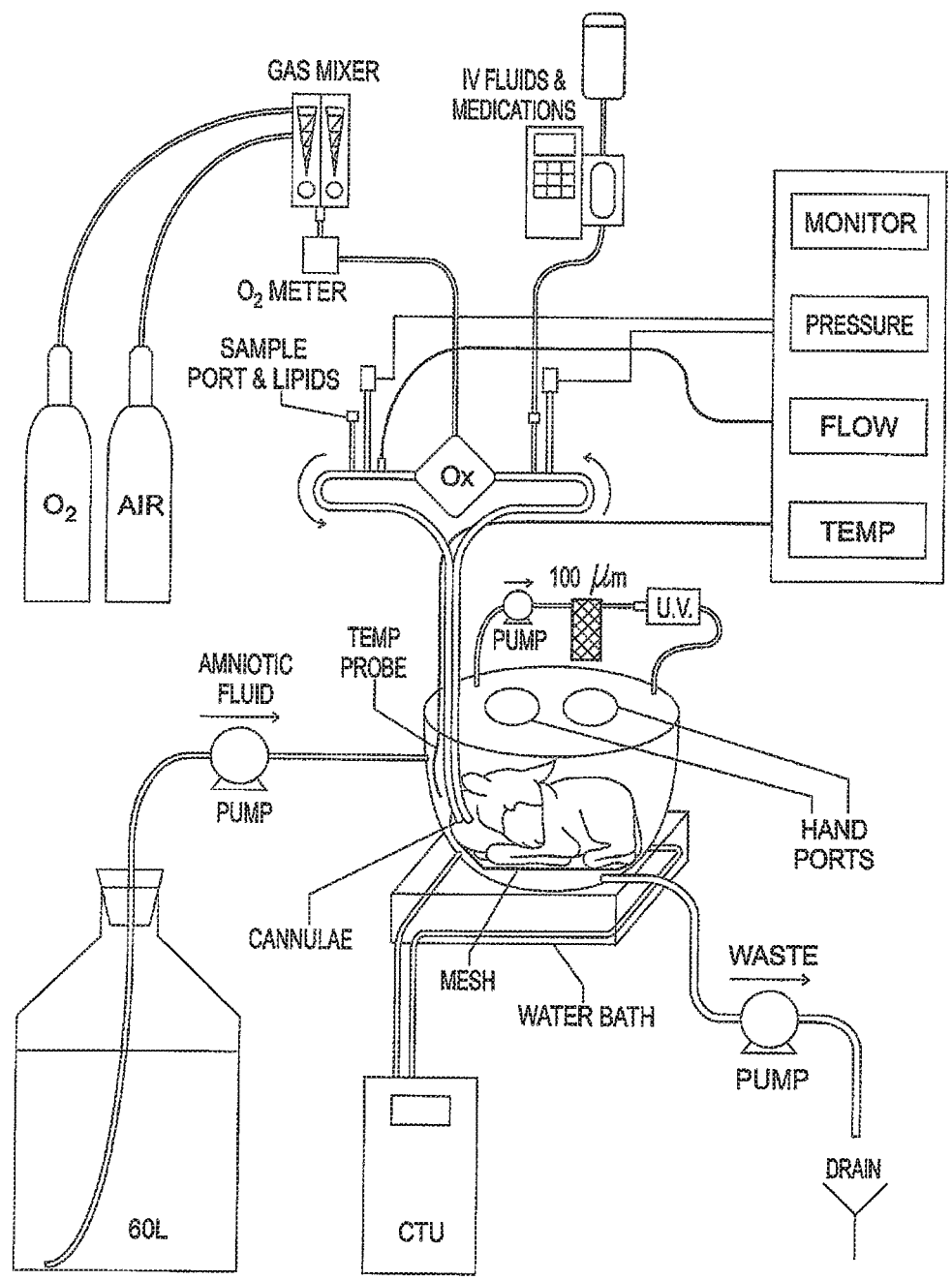
FIG. 7A provides a schematic diagram of an example of the apparatus of the instant invention.
Figure 7B:
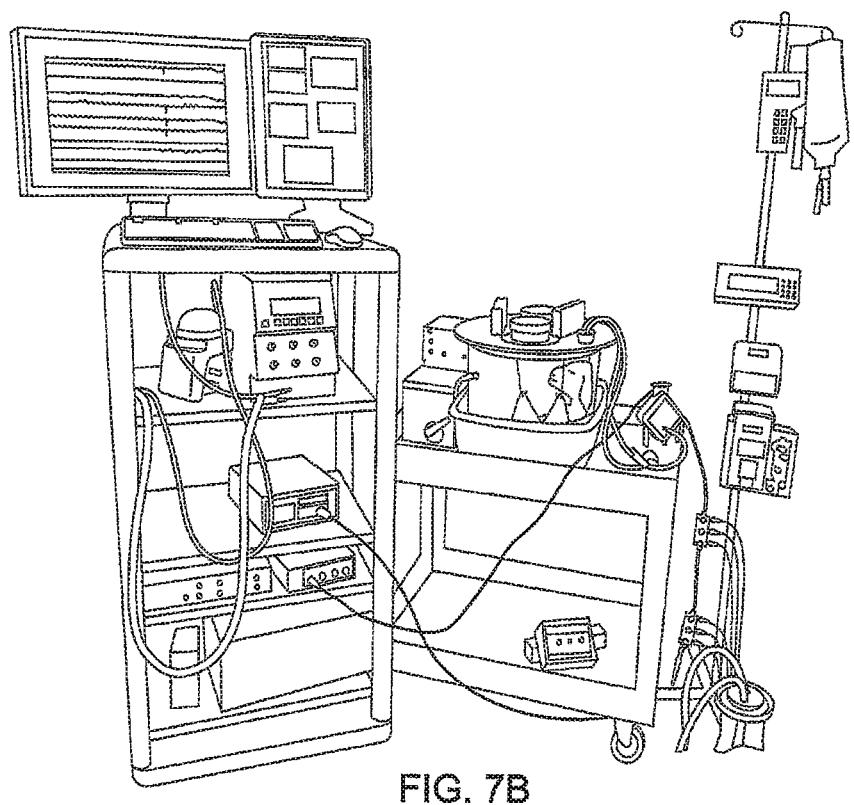
FIG. 7B provides an isometric representation of an example of the apparatus of the instant invention.

FIGS. 1 and 7 show examples of the apparatus of the instant invention. FIG. 7A provides a schematic of an example of an apparatus of the instant invention. The apparatus may be a single unit or comprise separate housing units with interconnecting tubing. Also, the apparatus shown is an appropriate size for a lamb. The apparatus can be sized appropriately for the size of the subject. For example, the apparatus may about ⅓ the size for a human subject.

Figure 2:
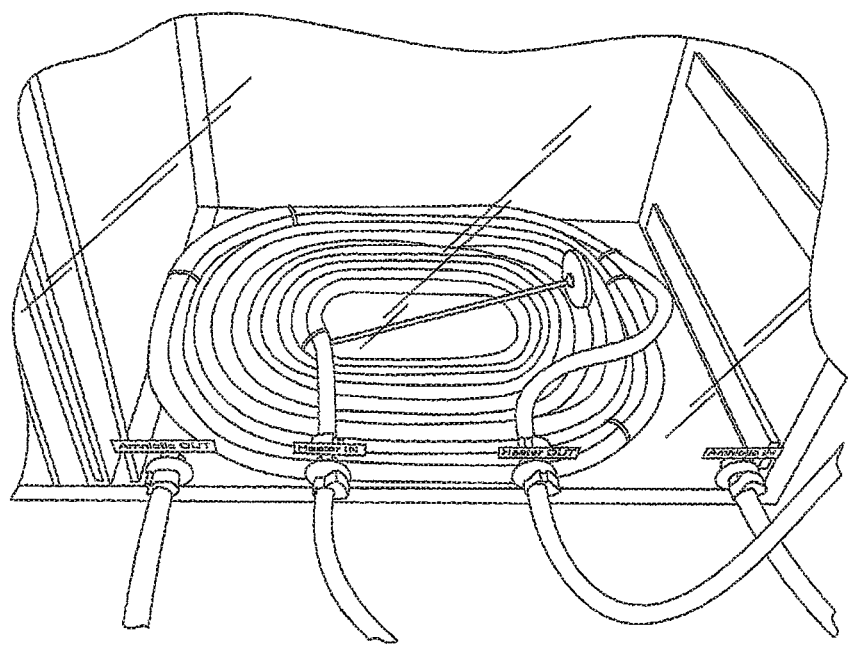
FIG. 2 is an isometric representation of an incubation chamber, the incubation chamber including four ports. Two of the ports are for circulation of a the sterile liquid in the chamber (labeled "amniotic in" and "amniotic out"). The other two ports are for circulating warm liquid into an enclosed unit within the chamber to maintain the subject's body temperature.

FIG. 2 provides a close-up of the incubation chamber. The incubation chamber may comprise any number of inlets and outlets. In a particular embodiment, the chamber comprises at least one inlet and one outlet to circulate the sterile liquid within. The incubation chamber may also comprise glove ports to allow sterile access to the subject (e.g., for swaddling of the subject to calm or to gain access to objects within the interior of the chamber). The chamber may also comprise at least one port for an IV line to the subject. The chamber may also have a variety of ports (e.g., resealable ports) to allow access for any of a variety of monitoring devices. For example, the chamber may have ports to allow access for an ultrasound device and/or a dialysis unit. The chamber may also comprise a UV light unit (e.g., to treat/inhibit jaundice).

Figure 3:
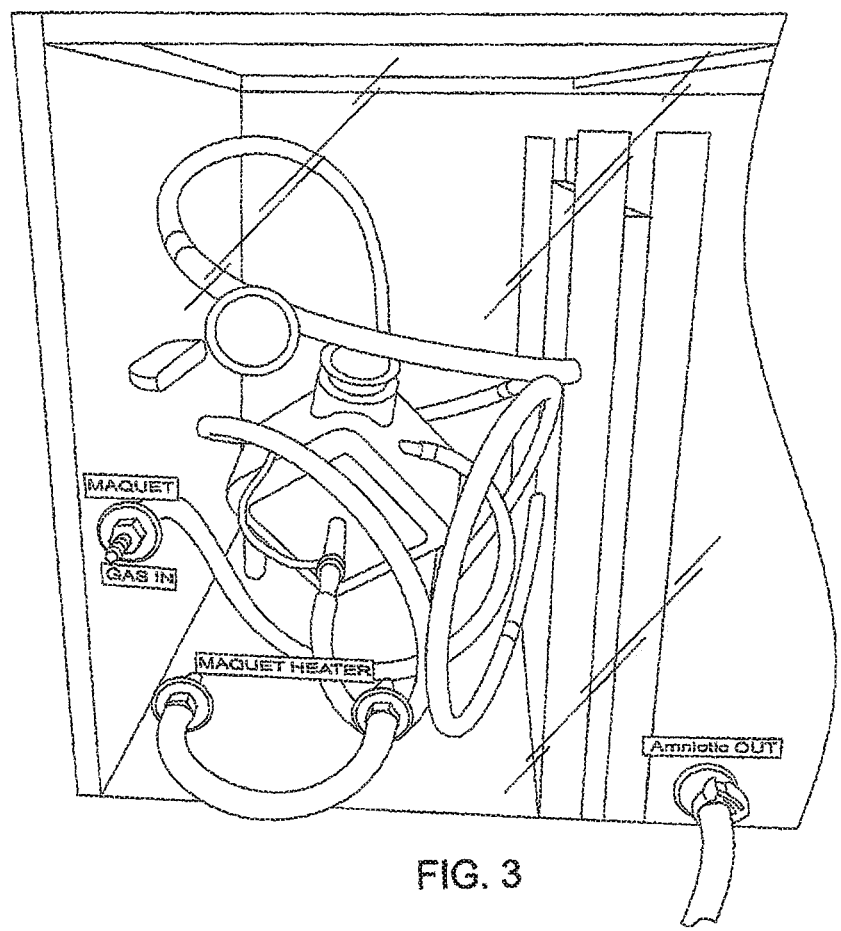
FIG. 3 is an isometric representation of an example of a dry chamber comprising an oxygenator.
Figure 5:
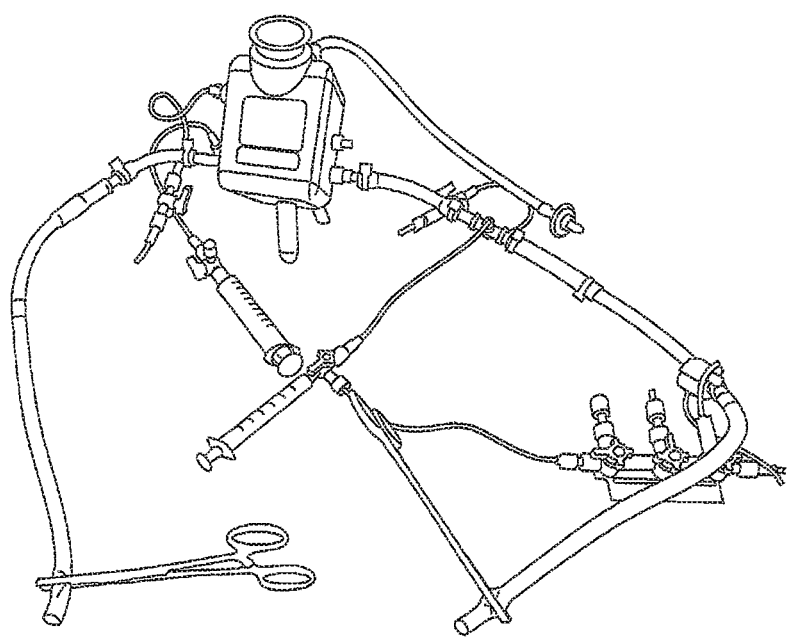
FIG. 5 is an isometric representation of a circuit design with the an oxygenator.
Figure 7C:
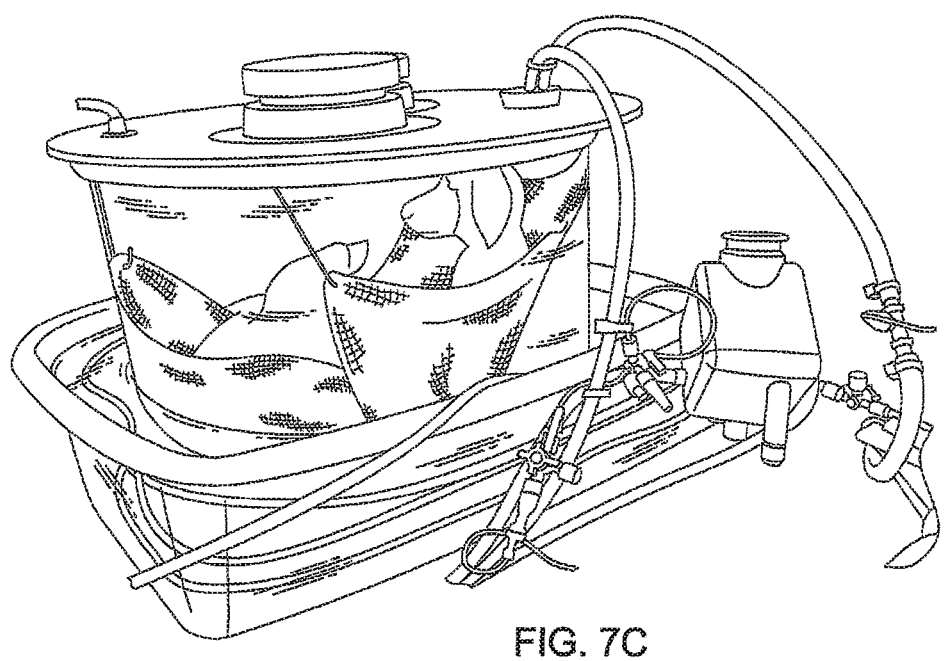
FIG. 7C provides an isometric representation of an example of the circuit of the apparatus of the instant invention.

FIG. 3 provides an image of the oxygenator contained within an optional dry chamber. FIGS. 5 and 7C show an example of the circuit design with the oxygenator without the dry chamber. While this chamber is shown as being separated from the incubator chamber by a divider in a single unit, the two can be separated into individual units (albeit connected by the necessary tubing and the like). The cannulas from the subject may connected directly to the oxygenator within the dry chamber or through ports in the dry chamber. The dry chamber may also comprise at least one port to attach the gas flow to the oxygenator. The port may connect to the oxygenator via tubing within the dry chamber. FIG. 3 also shows additional ports for the addition of a heater (e.g., via a warm liquid and tubing) to the dry chamber to help maintain the temperature of the blood being circulated through the tubing and the oxygenator. Additionally, the tubing to and/or from the oxygenator may be attached to monitors (e.g., temperature monitors, gas content monitors, etc.).

FIG. 7A provides a schematic of an example of an apparatus of the instant invention. The chamber is depicted as a bowl located within a water bath to maintain the temperature of the system. The incubation chamber is depicted with two glove/hand ports on the top of the chamber (though the ports could be located anywhere, including the sides of the chamber) for sterile access to the interior of the chamber. The chamber comprises an inlet port for the pumping in of sterile amniotic fluid and an exit port for the removal of used/old amniotic fluid. The chamber is also depicted as having a filtration system comprising a pump, at least one filter, and a UV filter for elimination of bacteria and contaminants. The chamber also depicts a mesh upon which the subject may be placed. FIG. 7A also depicts the oxygenator (Ox) in fluid connection with the blood system of the subject, particularly through cannulae into the neck vessels of the subject. The oxygenator is connected to a gas mixer drawing upon air and oxygen. The tubing of the oxygenator system may comprise at least one port for the introduction of compounds (e.g., nutrients, antibiotics, drugs, etc.) into the blood stream of the subject. Monitors such as for determining pressure, flow, and temperature may connected to the oxygenator system and/or the subject directly.

Definitions

The singular forms "a," "an," and "the" include plural referents unless the context clearly dictates otherwise.

As used herein, the terms "host," "subject," and "patient" refer to any animal, particularly mammals including humans.

The following examples are provided to illustrate various embodiments of the present invention. The examples are illustrative and are not intended to limit the invention in any way.

Example 1

Figure 6A:
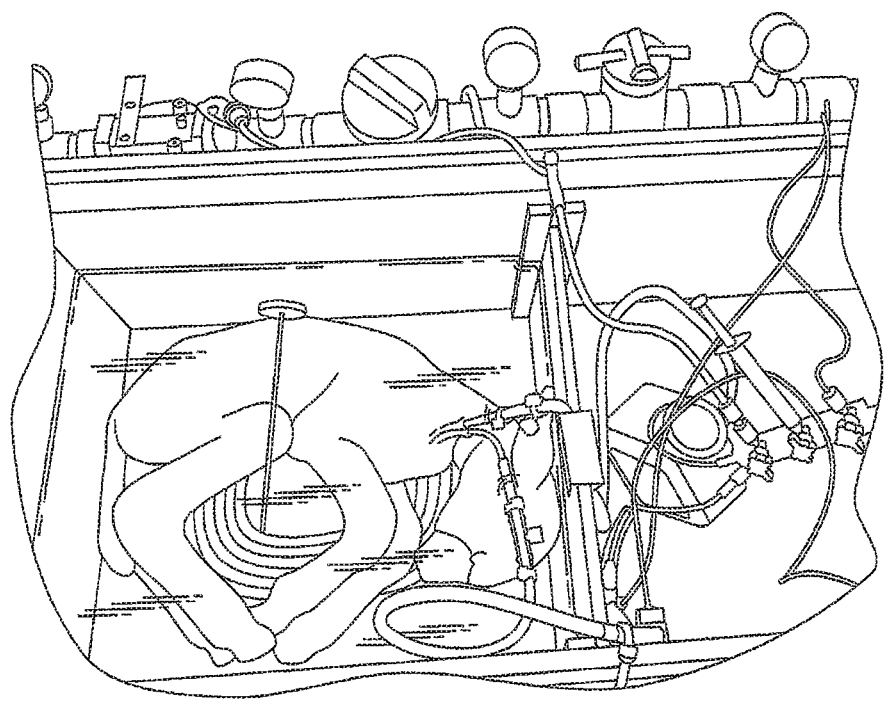
FIG. 6A is an isometric representation of a premature lamb connected to the apparatus of the instant invention.
Figure 6B:
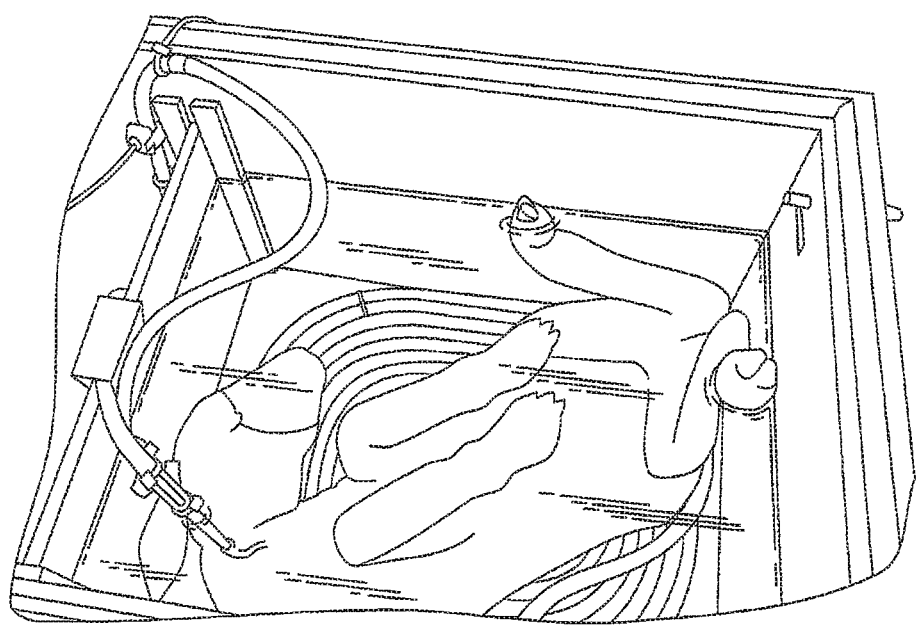
FIG. 6B is an isometric representation of the lamb after 5 days of growth.

A pre-term lamb (28 weeks) was maintained in the apparatus using the methods of the instant invention. 8 F to 10 F arterial ECMO cannulas were placed in carotid artery and internal jugular vein (size chosen at time of surgery). Approximately 12 inches of ECMO tubing was used on outflow and inflow to connect to the cannulae. The nutritional support provided was Total Parenteral Nutrition. FIG. 6A provides an image of the lamb connected to the apparatus and FIG. 6B shows the lamb after 5 days of growth. The growth of the premature lamb for five days demonstrates the ability of the instant invention to maintain a fetus outside of the womb.

Example 2

The complications of preterm birth result in significant morbidity and mortality, with one third of all infant deaths attributed to prematurity and chronic sequelae affecting most major organ systems in survivors. In 2010, 12.0% of all US births were preterm (less than 37 weeks completed gestation), and 3.5% were early preterm (less than 34 weeks gestation) (Martin et al. (2013) MMWR Surveill. Summ., 62(Suppl 3):136-138). Respiratory failure represents the most common and challenging problem faced by these patients, as gas exchange in critically preterm neonates is impaired by structural and functional immaturity of the lungs. Advances in neonatal intensive care including antenatal steroid administration, surfactant replacement, pulmonary vasodilatory therapy, and high-frequency oscillatory ventilation, have achieved improved outcomes and pushed the limitations of viability to the transition from the canalicular to the saccular phase of lung development at 22 to 24 weeks gestation. However, incomplete development of most major organ systems remains a limitation to survival and optimal functional outcomes in many patients. The development of an extrauterine system to support ongoing fetal growth and development without the perturbations induced by postnatal intensive care would offer a chance for survival of critically preterm infants, with potentially reduced mortality and long-term morbidity.

The concept of extracorporeal membrane oxygenation (ECMO) of the fetus is appealing due to the similarities to innate fetal physiology, in which extracorporeal gas exchange is performed by the placenta. The artificial placenta has been a subject of experimental trials since the 1960's, with a series of short experiments in which fetal lambs were cannulated via the umbilical vessels and perfused by first-generation bubble membrane oxygenators, with perfusion supported for 40 minutes to 2 days (Callaghan et al. (1963) Circulation 27:686-690; Zapol et al. (1969) Science 166:617-618). Due to substantial improvements in oxygenator and pump technology over the following two decades, the duration of extrauterine fetal life support has been increased using conventional pump-driven ECMO circuits, with runs lasting up to three weeks before onset of circulatory failure (Kuwabara et al. (1986) Artificial Organs 11:224-277; Kuwabara et al. (1989) Artificial Organs 13:527-531; Unno et al. (1993) Artificial Organs 17:996-1003; Unno et al. (1997) Artificial Organs 21:1239-1246). Despite these extensions in survival time, these studies were limited by circulatory overload and cardiac failure, resulting in the development of a fluid overloaded state and death of experimental animals.

Several features of the conventional pump-driven venous-arterial ECMO circuit are felt to represent challenges to the application of this technology to support of the fetus. The large priming volume of the circuit is substantially higher than the excess of the innate placental reserve, resulting in an increased volume of distribution. Pump-supported non-pulsatile flow also represents a departure from innate fetal physiology, with the potential for significantly increased cardiac afterload and resulting myocardial strain, in addition to a loss of innate autoregulation of flow. Finally, the large surface area of such circuits results in a requirement for high levels of systemic anticoagulation. A pumpless circuit may offer advantages over current ECMO technology including reduced priming and distribution volumes, shorter exposure of blood to thrombogenic surfaces, and achieving innate regulation of blood flow and pressure by the fetal heart itself.

The development of a pumpless extracorporeal oxygenation system remains elusive. Only five attempts to achieve fetal oxygenation in a pumpless system have been reported in the literature, and all were ultimately unsuccessful trials, with fetal demise within several minutes to up to 29 hours secondary to declining rates of blood flow and the requirement for pressor support to artificially prolong perfusion (Awad et al. (1995) J. Invest. Surg., 8:21-30, Reoma et al. (2009) J. Pediatr. Surg., 44:53-59; Mirua et al. (2012) Pediatr. Res., 72:490-494; Schoberer et al. (2014) Artificial Organs 38:208-14).

Recent technologic advances in extracorporeal membrane technology have resulted in the generation of exceptionally low resistance devices with low priming volume and highly efficient gas exchange, better recapitulating the properties of the placenta itself. In particular, the MaquetQuadrox-ID Pediatric Oxygenator supports the possibility of achieving pumpless oxygenation of fetal blood using the native heart to drive flow through the circuit. This oxygenator has been applied as a pumpless artificial lung in pediatric patients with good success (Boston et al. (2013) J. Thorac. Cardiovasc. Surg., 146:e42-e43). Herein, an approach was sought to maintain fetal blood oxygenation and stable hemodynamics using a modified pumpless circuit that permits the fetal heart to act as the pump, replicating innate fetal hemodynamics. Major challenges included achieving stable perfusion autoregulated by the innate fetal circulation, replicating the sterile fluid-immersed intrauterine environment, and facilitating appropriate fetal growth and development.

Herein, the first demonstration of pumpless extrauterine fetal life support (PEFLS) resulting in stable long-term incubation of the mammalian fetus for up to three weeks, with normal growth, metabolism, and maintenance of autoregulated fetal circulation is provided.

Methods

Surgical Procedure

Time-dated pregnant ewes were used at gestational ages 120 to 135 days (term=145 days). Animals were treated according to approved protocols by the Institutional Animal Care and Use Committee of the Children's Hospital of Philadelphia.

Ewes were anesthetized with 15 mg/kg of intramuscular ketamine, with maintenance of general anesthesia with 2-4% inhaled isoflurane in $O_2$. Intraoperative hemodynamic monitoring included pulse oximetry, with a constant infusion of isotonic saline administered via a central venous line placed in the right jugular vein to maintain maternal fluid balance.

A lower midline laparotomy was created to expose the uterus, with a small hysterotomy performed to expose the fetal sheep head and neck. In the setting of twin lambs, fetal blood was collected from the donor animal to prime the circuit. Donor animals underwent creation of a small right neck incision to expose the jugular vein, and were administered one intramuscular dose of buprenorphine (0.005 mg/kg) and one intravenous dose of sodium heparin (150 USP units, APP Pharmaceuticals, Schaumburg, Ill.), followed by creation of a small right neck incision to expose the jugular vein and placement of a catheter to permit collection of the entire blood volume of the animal. In the setting of singleton lambs, maternal blood was collected to prime the circuit. In all animals, maternal blood was collected and stored for subsequent transfusion requirements during the run.

Experimental lambs underwent creation of a small right neck incision to expose the carotid artery and jugular vein. Animals received one intramuscular dose of buprenorphine (0.005 mg/kg) and one intravenous dose of sodium heparin (300 USP units). After determination of the maximal cannula size accommodated by each vessel, ECMO cannulae were placed (size range 8-12 Fr, Avalon Laboratories, LLC, Rancho Dominguez, Calif.), with stabilizing sutures placed along the external length of cannulae at the neck. In a subset of animals, the external portion of the cannulas were fitted with a silicone 'sleeve' of 3-5 cm to permit increased tension of the stabilizing sutures. A subset of animals also underwent placement of insulated multi-stranded stainless steel wire electrodes to measure ocular electromyography (EOG) and electroencephalography (EEG) activities. EMG wire electrodes were implanted subcutaneously in the superior and inferior margins of the muscle overlying the orbit of one eye, and a pair of EEG electrodes were placed on the dura over the parasagittal parietal cortex and secured with cyanoacrylate glue, with a reference electrode sewn over the occiput.

Following construction and blood priming of the oxygenator circuit as described below, connection of the cannulas to the circuit was performed under continuous ultrasonographic visualization of the fetal heart. Occlusion of the umbilical cord was performed immediately following establishment of blood flow through the circuit, with administration of additional blood volume and/or atropine (0.1 mg) and/or epinephrine (0.1 mg) in a subset of animals demonstrating poor cardiac contractility immediately after establishment of circuit flow. After confirmation of stable cardiac function and circuit blood flow, stay-sutures were placed along the external length of the cannulas to secure them to the neck of the animal. Subsequently fetal lambs were weighed, washed in a warm sterile saline bath, and transferred to a sterile fluid incubator for further management as described.

In order to generate baseline data of the ovine fetus in utero, two time-dated pregnant ewes at 118 days gestational age underwent laparotomy for implantation of fetal vascular catheters and electrodes as described (Crossley et al. (1997) Reprod. Fertil. Dev., 9:767-73). Briefly, after induction of general anesthesia and exteriorization of the fetus, catheters were implanted in the fetal carotid artery and jugular vein, in addition to a reference catheter placed in the amniotic sac, followed by placement of EOG and dural EEG wire electrodes as described above. Additionally for these studies, EMG wire electrodes were placed in the nuchal and diaphragm muscles. The posterior left diaphragm was approached from a mid-axillary incision with two electrodes sewn 1.0 cm apart, while a single electrode was sewn into a long muscle of the neck to record nuchalactivity. Fetal catheters and electrodes were exteriorized through the maternal flank, and the uterus and abdomen were closed. Following a 48-72 hour recovery period, ewes were transferred to a holding cage for fetal monitoring.

Circuit

The pumpless extrauterine fetal life support (P-EFLS) circuit consisted of a low-resistance hollow fiber oxygenator (Quadrox-ID, Maquet, Rastatt, Germany) connected to the ECMO cannulae with 3/16" BIOLINE heparin-coated Medtronic tubing (Medtronic, Minneapolis, Minn.). Connections were established as an arterial-venous extracorporeal oxygenation circuit, with the carotid arterial outflow under pulsatile systemic pressure connected to the oxygenator inflow port and return flow connected to the outflow port. The priming volume was 81 mL, and heparinized fetal blood was used when available, with maternal blood utilized in singleton pregnancies. Circuit flow was measured with a flow probe (Transonic Systems Inc, Ithaca, N.Y.), and sweep gas supplied to the oxygenator was a blended mixture of medical air and oxygen titrated to fetal blood gas values.

Fluid Incubation

Trial incubator designs included a 30-liter heated stainless steel reservoir filled with sterile synthetic amniotic fluid ("still reservoir"), a 40-liter polycarbonate tank with continuous recirculation of fluid through a series of sterile filters ("recirculated filtration"), and finally a 60-liter tank within flow and outflow tubing mounted on a double-head peristaltic pump to facilitate continuous exchange of sterile fluid ("continuous exchange"). In the latter system, the complete volume of the tank is replaced three-fold with sterile inflow from a 180-liter reservoir over a 24-hour period. Synthetic amniotic fluid was composed of a balanced salt solution containing $Na^+$ (109 mM), $Cl^-$ (104 mM), $HCO_3^-$ (19 mM), $K^+$ (6.5 mM), $Ca_2^+$ (1.6 mM), pH 7.0-7.1, osmolarity 235.8 mOsm/kg water. Antibiotics were added to a final concentration of 18 mg/L gentamycin and 30 mg/L ciprofloxacin, and a submersible UV sterilizer pump was placed in the fluid reservoir continuous recirculated and sterilization throughout the run.

Fetal Lamb Maintenance on Circuit

Following stabilization and transfer of animals to the fluid incubator, a continuous infusion of heparin (80-200 USP units per hour) and prostaglandin E1 (0.1 mcg/kg/min, Pfizer Inc, New York, N.Y.) were administered intravenously. Blood was drawn every 1-4 hours for blood gas, electrolyte and coagulation values using an i-Stat® System (Abbott Point of Care Inc, Princeton, N.J.), with titration of the heparin infusion to a target Activated Clotting Time of 180-400 seconds (100-400 USP units per hour), and titration of the oxygenator sweep gas to target fetal partial pressures of $O_2$ ($PaO_2$ 20-30 mmHg) and $CO_2$ ($PaCO_2$ 35-45 mmHg) ($FiO_2$ 21-55%, sweep gas 0.125-1.5 L/min). Stored whole maternal blood was used to maintain fetal hemoglobin levels above 9 mg/dL. Analgesics (buprenorphine, 0.005 mg/kg IV every 3-5 hours as needed) and anxiolytics (midazolam, 0.4 mg/kg IV every 3-5 hours as needed) were administered during periods of perceived fetal distress (restless repetitive fetal movements, tachycardia, hypertension). Total parenteral nutrition was administered throughout the duration of fetal incubation, with a dosage of 3.5 g/kg amino acids (TrophAmine® 10%), 5-10% dextrose, and 3 g/kg lipids (Intralipid® 20%).

Data Acquisition

Fetal blood pressure, heart rate, circuit flow rates, transmembrane pressure differential, sweep gas flow rates, and bath fluid temperature were continuously recorded with input sampling every 0.1 seconds (LabChart 5, ADInstruments Inc, Colorado Springs, Colo.). Oxygen consumption and respiratory quotients were calculated daily, with measurement of the oxygenator exhaust gas content for oxygen and carbon dioxide. The following formulas were used:

Blood oxygen content $(O_2C)=1.34 \times Hgb \times SaO_2/100 + 0.003 \times PaO_2$ (mmHg) Oxygen Delivery (OD) =Post-membrane $O_2C \times$ Circuit Flow/100/body weight Oxygen Consumption (OC)=(Post-membrane $O_2C$–Pre-membrane $O_2C) \times$ Circuit Flow/100

Oxygen Extraction Rate (OER)=(OC/OD)×100.

Monitoring of catheterized fetal lambs in utero was started 48-72 hours after surgery and continued in 24-hour intervals on alternating days until completion of the experimental protocol at 140 days gestational age. Continuous polygraphic recordings of EEG, EMG and arterial pressures were recorded with data captured every 0.1 seconds (LabChart 5, ADInstruments Inc, Colorado Springs, Colo.).

Decannulation

Following completion of the planned incubation period, animals were transitioned from the fluid bath, with endotracheal intubation and suctioning to remove excess fluid from the lungs. General anesthesia was maintained with 2-4% inhaled isoflurane in 100% $O_2$, and intraoperative hemodynamic monitoring included pulse oximetry, with a constant infusion of isotonic saline administered via a peripheral venous cannula. The arterial and venous ECMO cannulas were removed with ligation of the vessels, and the neck incision was closed with a running absorbable suture. Anesthesia was then reversed, with animals extubated upon initiation of spontaneous respiration with arterial blood gases demonstrating adequate gas exchange ($PaO_2$>75 mmHg, $PaCO_2$<50 mmHg on inhaled medical air, $FiO_2$ 21%).

Results

Pilot Studies

A total of 5 pilot experiments were conducted to determine fetal stability on the PEFLS circuit (Table 1). Fetal gestational ages ranged from 120 to 140 days, with weights ranging from 3.20 to 4.89 kg. All animals demonstrated remarkable hemodynamic stability during support on the circuit, with no evidence of acidosis or increasing lactate, decreasing circuit flows, or circulatory failure. Unexpectedly, two animals displayed bradycardia immediately upon initial opening of fetal circulation onto the PEFLS circuit, requiring the administration of epinephrine and atropine to restore normal cardiac function. Following this initial event, no animals required vasopressor support at any time in the run. All animals were maintained on systemic anticoagulation and total parenteral nutrition.

TABLE 1

Study Animals.

| Animal Number - GA (weight, kg) | Length of Run (h) | Priming | Cannula Size | Average flow rate (SD) | Flow probe | Average pH (SD) | Fluid Incubation | Survived to decannulation | Complications during run | Pathology |
|---|---|---|---|---|---|---|---|---|---|---|
| 1 - 140 (3.62) (June) | 23 | Fetal | 8Fr (carotid) 8Fr (jugular) | 135.8 +/− MARCUS - check calibration | Transsonic T201; pre-oxygenator | 7.41 (7.28-7.62) | Still reservoir | No | Cardiac Arrest on opening circuit, bacterial infection of fluid | Closure DA, pulmonary inflammation, pulmonary hemorrhage |
| 2 - 135 (4.89) (Charlotte) | 71 | Maternal | 8Fr (carotid) 8Fr (jugular) | 336.3 (297-396) | Transsonic T201; pre-oxygenator | 7.24 (6.77-7.51) | Recirculated filtration | No | Cardiac arrest on opening circuit, bacterial infection of fluid bacteremia | Closure DA, diffuse pulmonary inflammation |
| 3 - 135 (3.49) (Lily) | 96 | Maternal | 12Fr (carotid), 10 Fr (jugular | 492.5 (450-520) | Transsonic T201; pre-oxygenator | 7.31 (7.10-7.56) | Recirculated filtration | Yes | Bacterial infection of fluid, bacteremia | Patent DA, diffuse pulmonary inflammation |
| 4 - 130 (4.24) (Little Alan) | 51 | Fetal | 10Fr (carotid), 12 Fr (jugular) | 435.6 (250-470) | Transsonic T201; post-oxygenator | 7.19 (6.60-7.46) | Continuous exchange | No | Clot formation circuit tubing, cardiac arrythmias, acidosis | Patent DA, diffuse shower emboli in lungs, heart, liver, bowel |
| 5 - 120 (3.20) (Eddie) | 108 | Maternal | 10Fr (carotid), 12 Fr (jugular) | 387.4 (290-430) | Transsonic H7XL; pre-oxygenator | 7.38 (7.24-7.57) | Continuous exchange | No | Traumatic decannulation | Normal organ histologyy |

Several obstacles to long-term fetal survival were identified, with bacterial contamination of the fluid incubator noted in four of five animals (Table 1). The initial pilot study employed a warmed open incubator filled with sterile amniotic fluid that was refilled only to compensate for evaporative losses, with no internal mixing and no antibiotics. Within 12 hours, this incubator fluid developed significant bacterial overgrowth, and after 23 hours on the circuit, the animal developed massive pulmonary hemorrhage. Histology confirmed significant diffuse inflammatory changes throughout the lungs, consistent with severe bacterial pneumonia. The fluid incubator was subsequently designed to a closed system with recirculation of amniotic fluid containing antibiotics (Ciprofloxacin 30 mg/L, Gentamycin 18 mg/L) through a series of filters with increasingly fine pore size (1 mm, 10 μm, 5 μm, 2 μm, 0.2 μm) to eliminate gross debris and maintain sterility. Two studies were performed with this fluid incubator. In both cases, bacterial growth was confirmed on culture of sampled bath fluid within 48 hours of incubation. One animal developed increasing $FiO_2$ requirements over the course of the incubation period and was found on echocardiography to have significant constriction of the ductusarteriosus, resulting in impaired mixing of oxygenated blood via the superior vena cava. The second animal had no complications during the 96-hour incubation period and was delivered and decannulated at 140 days gestational age (term), but was found to have inadequate gas exchange despite vigorous spontaneous respiratory effort. Both animals were found to have significant pulmonary inflammation consistent with pneumonia as well as bacteremia. A closed sterile system with continuous fluid exchange was designed, with synthetic amniotic fluid passing through a series of 0.22 μm filters to enter the incubator, with the rate of inflow matched to outflow and complete exchange of the 60 liter incubator volume 2-4 times daily (FIG. 7).

Additional technical limitations identified included premature closure of the ductusarteriosus in two animals exposed to epinephrine, clot formation in a circuit including a segment of non-antithrombogenic-coated tubing, and traumatic decannulation in one animal with resulting hemorrhagic demise (Table 1). These findings led to the addition of a continuous infusion of prostaglandin-E2 for maintenance of fetal shunts, implementation of a circuit employing exclusively antithrombogenic-coated tubing, and the addition of a sterile silicone sleeve overlay on each cannula to permit increased stabilization of anchoring stay-sutures.

Fetal Biochemical and Hemodynamic Parameters

Following implementation of the system refinements noted above, five experimental animals were maintained on the PEFLS circuit for 343.8+/−93.5 hours (Table 2). Trends in fetal blood gases, hemodynamics and circuit flow rates over the course of five independent experiments are summarized in FIG. 8. The pH remained stable throughout the duration of the incubation period (FIG. 8A), and the partial pressures of oxygen and carbon dioxide were maintained at target fetal levels throughout the course of the experiment (FIG. 8B). While the basal heart rate was stable throughout the duration of incubation (FIG. 8C), the animals' systolic blood pressure increased steadily (FIG. 8D), consistent with expected rates of growth. Similarly, circuit flow rates increased in proportion to the increase in blood pressure (FIG. 8E), and the concentration of supplied oxygen required to maintain target arterial blood oxygenation levels increased steadily as well, reflecting increased fetal metabolic demand (FIG. 8F).

TABLE 2

Study Animals

| Animal Number - GA (weight, kg) | Length of Run (h) | Priming | Cannula Size | Average flow rate (SD) | Average pH (SD) | GA at decannulation (weight, kg) | Complications during run | Outcome and Pathology |
|---|---|---|---|---|---|---|---|---|
| 1-125 (3.17) (Willow) | 209 | Fetal | 10Fr (carotid) 10Fr (jugular) | 350.7 +/− 137.2 | 7.38 +/− 0.21 | 134 (3.9) | Hypotension after initiation of midazolam infusion with resulting period of hypoxia >8 hours | Appropriate gas exchange on ventilator support with good spontaneous respiratory effort. Euthanized DOL2 - generalized hypotonia. Pathology: normal organ history. Appropriate lung maturation. |
| 2-120 (3.20) (Seinne) | 360 | Fetal | 10Fr (carotid) 12Fr (jugular) | 380.1 +/− 154.7 | 7.34 +/− 0.27 | 135 (4.2) | Bacterial overgrowth in fluid incubator | Appropriate gas exchange on ventilator support with good spontaneous respiratory effort. Euthanized DOL1 due to inability to wean from ventilator. Pathology: extensive pulmonary inflammation, mucus plugging of distal airways. Appropriate lung maturation. |
| 3-120 (3.30) (Bowie) | 372 | Maternal | 10Fr (carotid) 12Fr (jugular) | 374.6 =/− 149.9 | 7.40 +/− 0.32 | 136 (4.5) | Bacterial overgrowth in fluid incubator | Abrupt onset of hypotension following the development of lactic acidosis associated with fluid incubator infection. Euthanized DOL0 due to severity of acidosis. Pathology: mild pulmonary inflammation. Appropriate lung maturation. |
| 4-120 (3.20) (Iggy) | 288 | Maternal | 10Fr (carotid) 10Fr (jugular) | 390.6 +/− 201.2 | 7.47 +/− 0.29 | 134 (3.7) | Small cannulableed (suture trauma) | Long-term survivor; MRI head/chest/abdomen: normal organ structures |
| 5-120 (2.9) (Manson) | 490 | Maternal | 10Fr (carotid) 12Fr (jugular) | 334.2 +/− 121.2 | 7.48 +/− 0.17 | 140 (4.12) | GI hemorrhage following systemic anticoagulation, resulting in complete post-natal bowel obstruction. | Appropriate gas exchange on ventilator support with good spontaneous respiratory effort. Euthanized DOL4 due to inability to wean from ventilator. Histology: |

Flow Characteristics on PEFLS

Figure 9:
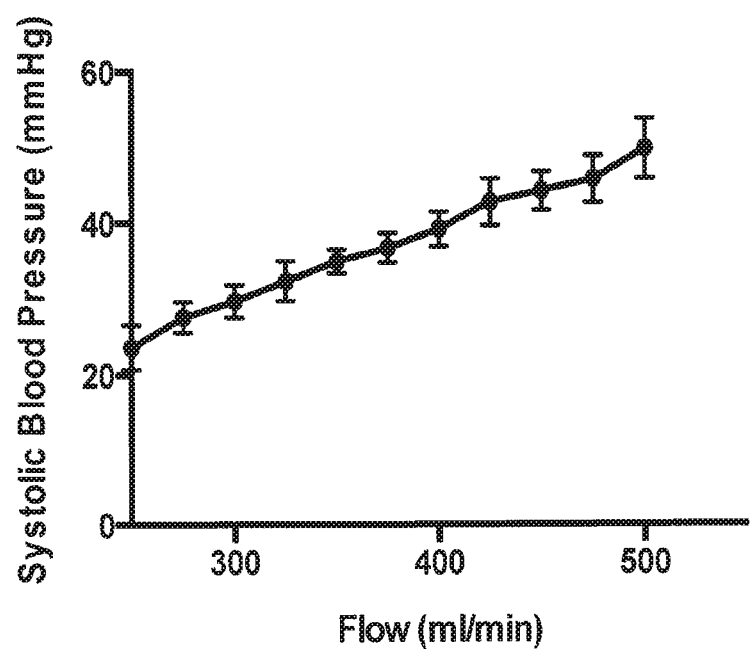
FIG. 9 provides a graph showing a linear relationship between systolic blood pressure (mmHg) and circuit flow rates (ml/min). Error bars represent four independent experiments.

Fetal flows during PEFLS are linearly related to the systolic blood pressure of the animal (FIG. 9) and are pulsatile and directly correlate with the measured cardiac output. Autoregulation of circuit flow was consistently demonstrated in response to hypoxia, with compensatory increases in systolic blood pressure and circuit flow in response to reduced sweep gas flow to the oxygenator and normalization to baseline flow and blood pressure after restoration of sweep gas flow.

Fetal Growth and Metabolism in PEFLS

Over the course of five independent experiments ranging from 209 to 490 hours, animals gained an average of 930+/−278 grams (FIG. 10A). Fetal breathing movements were noted regularly throughout the incubation period, and were correlated with the partial pressure of carbon dioxide measured in the systemic circulation (FIG. 10B). Echocardiography was performed to confirm patency of fetal circulatory shunts, including the ductusarteriosus (FIG. 10C). Total oxygen consumption increased steadily over the course of five independent experiments (FIG. 10D), consistent with growth and proportionate increases in fetal metabolic demand. Following normalization to estimated fetal weight as extrapolated from the growth curve generated from pre- and post-PEFLS weights, oxygen consumption rates were found to remain stable throughout the course of incubation.

Sleep-wake cycles, breathing movements and whole-body movements were recorded in two chronically catheterized fetal lambs by EEG, EOG and EMG, and compared to two lambs maintained in the artificial placenta over the same range of gestation. Recordings from a catheterized fetal lamb in utero were made at 125 and 140 days gestational age, and recordings from a fetal lamb in the artificial placenta were made at the same gestational ages. A developmental progression from fragmented to consolidated sleep between the two gestational ages is apparent in both in utero and PEFLS animals.

Figure 11A:
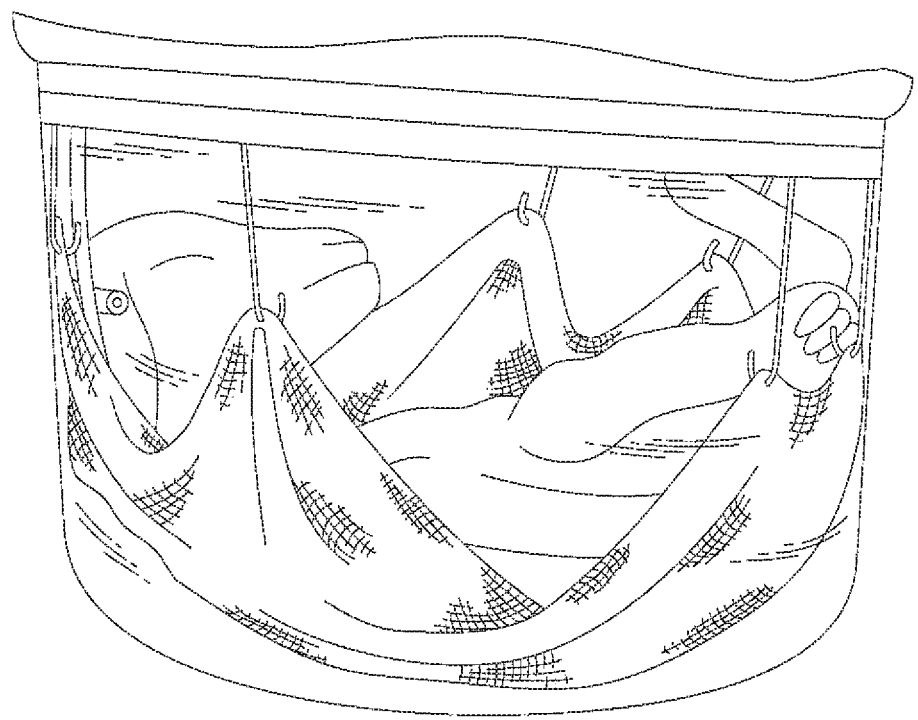
FIG. 11A shows growth and development of the lamb, specifically a representation of the fetal lamb on day 1 (GA 120 days).
Figure 11B:
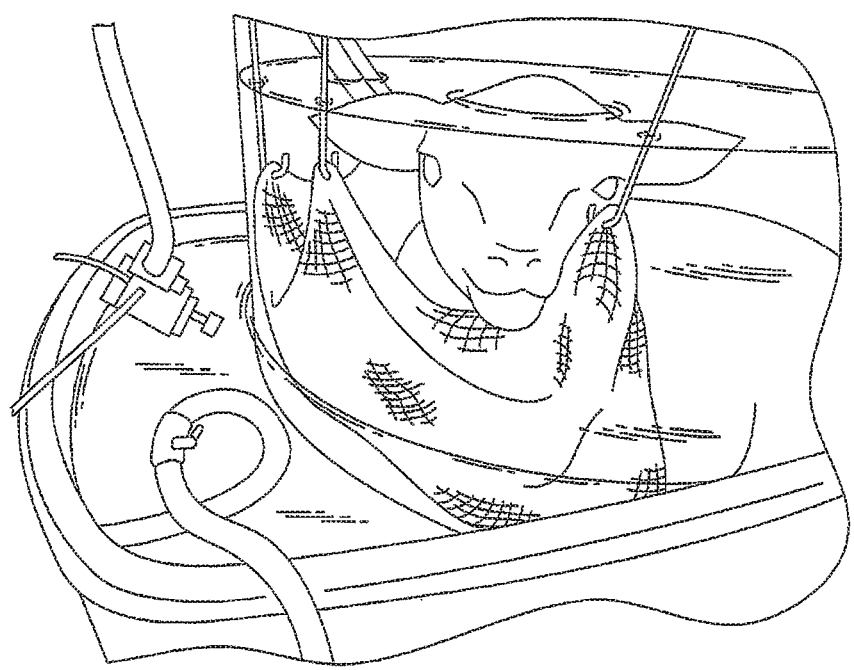
FIG. 11B shows growth and development of the lamb, specifically a representation of the fetal lamb on day 14 (GA 134 days).
Figure 11C:
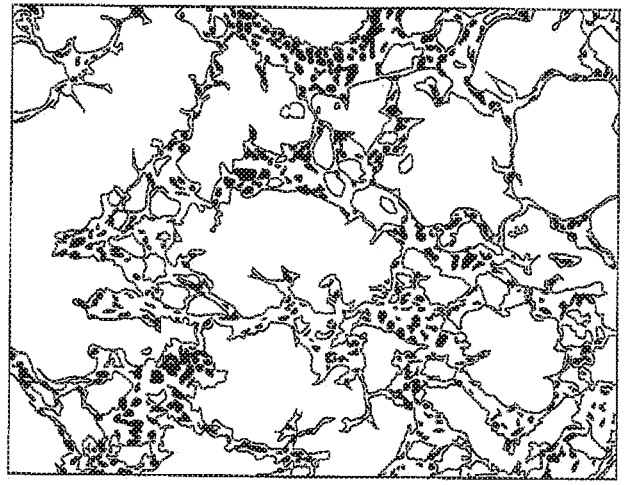
FIG. 11C shows growth and development of the lamb, specifically an image of hematoxylin and eosin (H&E) staining of paraffin-embedded fetal lung following day 14.
Figure 11D:
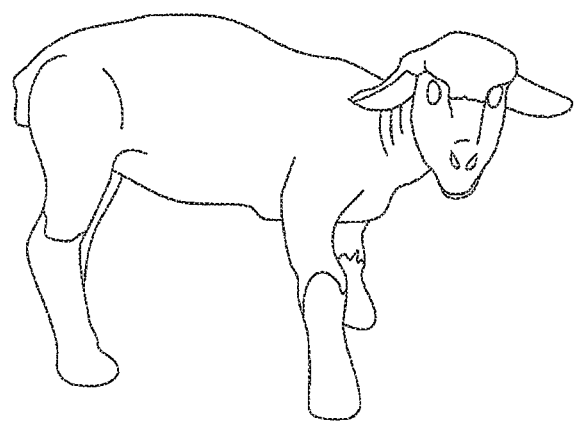
FIG. 11D shows growth and development of the lamb, specifically a representation of normal growth and development of the lamb 6 months after incubation.

Fetal growth and development was consistently observed over the course of the incubation period, with the eyelids noted to progress from fused to open, increased wool growth, and increased level of activity and alertness (FIGS. 11A and 11B). Histologic evidence of lung maturation was also consistently demonstrated, with thinning of the alveolar walls and secondary septations acquired upon completion of PEFLS runs over 200 hours compared to control lungs of 120 day gestation lambs (FIG. 11C, Table 2).

One animal was maintained for 288 hours in the absence of infection, and was successfully delivered from the artificial placenta and transitioned to postnatal life (FIG. 5D). Magnetic resonance imaging confirmed normal structure of the brain, thoracic and abdominal viscera, and the animal displayed appropriate growth and development over eight months before transport to a long-term adoptive facility.

A pumpless circuit to permit long-term support of the extrauterine fetus may be the optimal design for an artificial placenta. However, previous efforts have been limited by low flow rates and poor perfusion. Herein, a system for pumpless extrauterine fetal life support (PEFLS) is described which results in stable long-term incubation of the mammalian fetus for up to three weeks or more. By employing a superior oxygenator with extremely low resistance and low priming volumes, a circuit has been created which more closely approximates the placenta itself The reported placental blood volume of the sheep is 23.1 to 48.1 ml/kg (Creasy et al. (1970) Circ. Res., 27:487-494), with placenta blood flow reported as 199+/−20 ml/min/kg (Faber et al. (1972) J. Pysiol., 223:375-393). The circuit described herein requires a priming volume of 80 to 90 mls, or 27 ml/kg of an average 120-day 3 kg fetal lamb, and flow rates in the system averaged 120-140 ml/min/kg.

In applications of extracorporeal oxygenation to the fetus, priming of the oxygenator circuit with fetal blood might provide advantages with respect to oxygen unloading and maintaining peripheral perfusion. However, priming of the circuit was completed with fetal blood in the case of twin gestations and with maternal blood in the event of singleton lambs (Tables 1 and 2), and no differences were observed in arterial oxygen content, lactic acid production, or cardiac function over the course of long-term fetal incubation.

A pumpless circuit in which innate hemodynamics can be maintained by autoregulation may be advantageous for normal fetal development. Prior to the instant invention, the longest extrauterine fetal incubation experiments was with animals maintained on a circuit employing a silicone hollow fiber membrane oxygenator and a roller pump and animals cannulated via the umbilical vessels (Kuwabara et al. (1986) Artificial Organs 11:224-277; Kuwabara et al. (1989) Artificial Organs 13:527-531). In 6 animals maintained with the fetal circulation under direct regulation of the roller pump, the maximum duration of incubation was 8 hours, with rapid onset of cardiac failure accounting for fetal demise in the majority of experiments. Run times were significantly prolonged in this study by the addition of a blood reservoir, which was filled passively by the umbilical arterial outflow, and which automatically regulated flow rates through the pump according to the rate of reservoir filling. Flow rates were maintained between 100 to 200 ml/min in all animals, with fetal gases maintained within target ranges throughout the incubation period. Although not a pumpless system, this modification did permit flow rates to better mirror the innate circulation, and did extend survival time to up to 165 hours. However, ultimately cardiac failure and subcutaneous edema developed in all animals which did not succumb to iatrogenic complications such as bleeding or embolism. In a subsequent study, this reservoir-supported circuit was modified by the addition of hemodialysis to improve fluid and electrolyte balance, achieving incubation lengths of up to 236 hours with flow rates between 50 to 100 ml/min/kg. Again, while three animals died due to catheter malfunctions, cardiac failure was the cause of all non-technical deaths, with progressive circulatory depression and eventual demise on the circuit. Based upon the suspicion that fetal movement may have contributed to fluid imbalance, flow disturbances and bleeding complications, a follow-up study employing this circuit with the administration of continuous paralytics resulted in the stable support of two preterm goat fetuses for 494 and 543 hours respectively, with flow rates between 80 to 180 ml/min/kg and successful delivery from the incubator to mechanical ventilation (Unno et al. (1993) Artificial Organs 17:996-1003). However, animals failed to demonstrate adequate spontaneous respiratory effort and expired due to respiratory insufficiency. Further analyses of the performance of this circuit, with modifications including the placement of an occlusion tube to create a fixed point of resistance on the arterial outflow, achieved incubation times up to 236 hours, but all animals died due to circulatory failure characterized by declining flows and blood pressure as well as recurrent arrhythmias (Unno et al. (1997) Artificial Organs 21:1239-1246).

Additional studies attempting to achieve improved circulatory outcomes following prolonged extrauterine fetal incubation resulted in similar findings of demise due to circulatory failure. In 1998, four goat fetuses cannulated via the umbilical vessels and maintained on a circuit comprised of a hollow fiber oxygenator and a centrifugal pump were studied (Yasufuku et al. (1998) J. Pediatr. Surg., 33:442-448). This circuit permitted the delivery of pulsatile flow at higher rates compared to previous published reports, with flow rates ranging from 113 to 193 ml/min/kg. The total duration of support ranged from 87 to 237 hours, with all animals succumbing to hydrops secondary to circulatory failure. In 2002, 12 goat fetuses cannulated via the umbilical vessels and supported by a circuit employing a roller pump with manual control of the flow rate, in an attempt to increase the rate of umbilical artery drainage, were studied. In this study, 3 animals died due to cannula problems and one due to hypoxia secondary to clot formation in the circuit, while the remaining 8 animals developed circulatory failure. Flows ranged from 103.0+/−17.0 to 176.0+/−15.0 (ml/min/kg) and adequate gas exchange was achieved, however drainage of the umbilical artery by the roller pump was felt to impose increased afterload to the myocardium.

The continued demonstration of circulatory overload in pump-supported fetal ECMO suggests an unacceptable afterload imposed by these circuits, resulting in eventual cardiac insufficiency. Moreover, the ideal artificial placenta will permit the fetus to maintain circulation analogous to that achieved in the intact fetal-placental unit, where perfusion is determined by fetal cardiac output. However, previous attempts to design a pumpless system for fetal perfusion have yielded discouraging results. For example, the use of a pumpless circuit in a series of lambs with surgically created congenital diaphragmatic hernias was reported (Awad et al. (1995) J. Invest. Surg., 8:21-30). Animals were perfused for up to 6 hours, but circuit flow rates did not exceed 75 ml/min and oxygenation levels were inadequate to sustain stable long-term incubation. In 2009, a pumpless extracorporeal circuit using a hollow-fiber oxygenator and umbilical cannulation in four near-term lambs was reported (Reoma et al. (2009) J. Pediatr. Surg., 44:53-59). Animals were supported for up to four hours in this system, with a gradual decline in circuit flows and systolic blood pressure over this short course of incubation. It was concluded that a pump-driven system would be required to maintain adequate flow and perfusion of the fetus. In 2012, a pumpless extracorporeal circuit in lambs at a gestational age of 130+/−1.6 days, with cannulation of a single umbilical artery and the umbilical vein, was reported (Mirua et al. (2012) Pediatr. Res., 72:490-494). The 5 animals studied survived for an average of 18.2+/−3.2 hours, but developed a progressive lactic acidosis resulting in cardiac failure and death. Administration of pressors to increase cardiac contractility and ionotropes to induce peripheral vasodilation did not achieve long-term survival in this system. Lastly, the development of a miniaturized low-volume oxygenator, with a priming volume of 12 mL and gas exchange surface area of 0.12 $m^2$, was reported (Schoberer et al. (2014) Artificial Organs 38:208-14). Animals were cannulated via the umbilical vessels but were maintained on mechanical ventilation in addition to extracorporeal oxygenation. In this system, 6 of the 7 animals studied were maintained on pumpless extracorporeal support for 6 hours, the defined endpoint, however all animals developed a metabolic acidosis, elevated blood lactate, and a continuous decline in blood pressure, and three animals ultimately required catecholamines to reach the experimental endpoint. In the system of the instant invention, no animals required pressor support at any time to maintain stable hemodynamics and perfusion over up to three weeks of support.

Long-term sterility of the fetal fluid incubation system was achieved in this study. Previous reports employing fluid immersion systems have not extensively described rates of bacterial contamination and strategies to improve sterility. Notably, an incubator filled with synthetic amniotic fluid and antibiotics, with daily in-line filtration and complete exchange every other day, has been described (Kuwabara et al. (1989) Artificial Organs 13:527-531). In this study, the longest duration of fetal incubation was 236 hours. In the instant study, with the final incubator design, infection did not commonly occur before day 12, or 288 hours. The prolonged length of the incubation periods likely increases the difficulty in maintaining sterility. Several refinements of the incubator design were made throughout the series of experimental animals, including the addition of a mounted glove to facilitate manipulation and position changes of the animal without breaching sterility, as well as the placement of an internally-fixed and sealed suction device to permit removal of waste products and debris. In addition, an aquarium model UV filtration system was placed within the fluid reservoir to provide an additional level of antimicrobial protection. With these modifications, sterility was maintained for up to three weeks of fetal incubation, representing a significant period for growth and development of a critically preterm infant.

One advantage of a pumpless system for fetal perfusion is the maintenance of regulation of cerebral blood flow by innate autoregulatory pathways. Ensuring adequate oxygenation of the developing brain is a key consideration in the design of an artificial placenta, with cerebral autoregulation felt to represent one important component of cerebral perfusion. Cerebral autoregulation has been well described in the population of neonatal infants who require intensive care, but is poorly understood. Significant individual variability exists with respect to measured ranges of cerebral artery blood flow rates, vasoreactivity, and autoregulatory thresholds, to the extent that normative values for these patients remain undefined (Vutskis, L. (2014) Pediatr. Anesth., 24:22-29). Cerebral autoregulation has also been observed in the human fetus, with increased middle cerebral artery peak systolic velocity described in fetuses with intrauterine growth restriction (Hanif et al. (2007) Am. J. Perinatol., 24:501-505). The effects of conventional pump-supported ECMO on cerebral perfusion in neonates have demonstrated a well-documented loss of autoregulation in response to fetal hypoxia in a number of systems, including lamb models of veno-arterial ECMO (Short et al. (1993) Pediatr. Res., 33:289-294; Stolar et al. (1988) J. Pediatr. Surg., 23:1163-1168), studies of newborn lambs supported on veno-venous ECMO (Walker et al. (1996) Crit. Care Med., 24:2001-2006), as well as infants supported on veno-arterial ECMO (Papademetriou et al. (2013) Adv. Exp. Med. Biol., 765:203-209), suggesting significant alterations in cerebral perfusion in the setting of pump-supported ECMO flow. Notably, numerous studies indicate that the long-term neurodevelopmental impact of ECMO is impaired functional outcome in these patients (Kumar et al. (1994) Pediatrics 93:951-955; Iisselstiin et al. (2014) Semin. Perinatol., 38:114-121). In the instant study, EEG studies revealed waveforms consistent with those observed in chronically catheterized lambs in utero. Maintenance of cerebral autoregulation likely achieves optimal brain perfusion and development in the artificial placenta, improving outcomes in this population with potentially devastating neurodevelopmental sequelae following conventional management.

The implications of the total extrauterine fetal life support (TEFLS) system extend beyond clinical innovations, and provide a basis for addressing fundamental questions regarding the role of the placenta in fetal development. For the first time, long-term stable maintenance of a fetus amputated from the maternal-placental axis has been achieved, making it possible to study the relative contribution of this organ to fetal maturation. The system can also be used to bridge the transition from fetal to postnatal life, which may be applied to models of congenital lung disease to expand the window of opportunity for therapeutic interventions. The TEFLS system therefore represents a capability that has not been previously available for research in fetal physiology, and represents a powerful new resource for numerous translational clinical applications.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed:

1. A method for supporting a human premature fetus in an extrauterine life support system, the method comprising the steps of:
cannulating the premature fetus to a pumpless oxygenation circuit such that the pumpless oxygenation circuit defines a premature fetus blood path that includes a first portion that provides blood outflow from the premature fetus to an inflow port of an oxygenator, a second portion that passes through the oxygenator from the inflow port to an outflow port of the oxygenator, and a third portion that provides return blood flow from the outflow port to the premature fetus;
positioning the premature fetus inside an incubation chamber;
sealing the incubation chamber with the cannulated premature fetus inside the incubation chamber to form a water-tight internal environment for the premature fetus;
transferring a synthetic amniotic liquid from a supply tank defining a first volume into the incubation chamber defining an internal incubation chamber volume, the first volume being greater than the internal incubation chamber volume;
submerging the premature fetus in the synthetic amniotic liquid inside the incubation chamber;
priming the oxygenator with either fetal or maternal blood;
circulating fetal blood from the premature fetus to the oxygenator and back from the oxygenator to the premature fetus through the pumpless oxygenation circuit wherein the circulating fetal blood is pumped by the premature fetus; and
periodically draining at least a portion of the synthetic amniotic liquid from the incubation chamber and in response to the draining step transferring fresh synthetic amniotic liquid from the supply tank into the incubation chamber.

2. The method of claim 1 further comprising flowing an oxygen-containing sweep gas into the oxygenator and flowing an oxygenator exhaust gas from the oxygenator.

3. The method of claim 2 wherein the oxygen-containing sweep gas has an oxygen content and further comprising monitoring the oxygen content of the oxygen-containing sweep gas.

4. The method of claim 3 wherein the oxygenator exhaust gas has an oxygen content and further comprising monitoring the oxygen content of the oxygenator exhaust gas.

5. The method of claim 4 wherein the oxygen-containing sweep gas has a flow rate into the oxygenator and further comprising monitoring the flow rate of the oxygen-containing sweep gas into the oxygenator.

6. The method of claim 5 further comprising calculating an oxygen consumption across the oxygenator.

7. The method of claim 6 wherein the oxygenator exhaust gas has a carbon dioxide content and further comprising monitoring the carbon dioxide content of the oxygenator exhaust gas.

8. The method of claim 6 wherein the oxygen-containing sweep gas is a blended gas mixture of gaseous oxygen supplied from an oxygen gas source and gaseous air supplied from an air gas source.

9. The method of claim 6 further comprising the step of removing fetal waste products from the sealed incubation chamber via a suction device through a water-tight seal on the incubation chamber wherein the step of removing fetal waste products is accomplished without opening the sealed incubation chamber.

10. The method of claim 6 wherein the incubation chamber is a medical grade plastic bag or sac.

11. The method of claim 6 wherein the oxygenator is a polymethyl pentene hollow fiber membrane oxygenator.

12. The method of claim 6 wherein the first portion of the pumpless oxygenation circuit includes a cannula and tubing wherein the tubing is about 12 inches or less and extends between the cannula and the oxygenator.

13. The method of claim 1 further comprising the step of removing fetal waste products from the sealed incubation chamber via a suction device through a water-tight seal on the incubation chamber wherein the step of removing fetal waste products is accomplished without opening the sealed incubation chamber.

14. The method of claim 1 wherein the incubation chamber is a medical grade plastic bag or sac.

15. The method of claim 1 wherein the oxygenator is a polymethyl pentene hollow fiber membrane oxygenator.

16. The method of claim 1 wherein the first portion of the pumpless oxygenation circuit includes a cannula and tubing wherein the tubing is about 12 inches or less and extends between the cannula and the oxygenator.

* * * * *